US007361789B1

(12) United States Patent
Yan et al.

(10) Patent No.: US 7,361,789 B1
(45) Date of Patent: Apr. 22, 2008

(54) DIHYDRONAPHTHALENE COMPOUNDS, COMPOSITIONS, USES THEREOF, AND METHODS FOR SYNTHESIS

(75) Inventors: Qi Yan, Oak Park, CA (US); Carlos Orihuela, Westlake Village, CA (US); Bo Shen, Thousand Oaks, CA (US); Ying Chen, Thousand Oaks, CA (US); Xin Wang, Thousand Oaks, CA (US); John Ng, Oak Park, CA (US); Ruizhi Ji, Thousand Oaks, CA (US); Pengzu Zhou, Thousand Oaks, CA (US)

(73) Assignee: Amgen Inc., Thousand Oaks, CA (US)

( * ) Notice: Subject to any disclaimer, the term of this patent is extended or adjusted under 35 U.S.C. 154(b) by 243 days.

(21) Appl. No.: 11/191,892

(22) Filed: Jul. 27, 2005

Related U.S. Application Data

(60) Provisional application No. 60/591,624, filed on Jul. 28, 2004.

(51) Int. Cl.
*C07C 211/03* (2006.01)
*C07C 209/26* (2006.01)
*C07C 209/28* (2006.01)

(52) U.S. Cl. .................. 564/337; 564/338; 564/396; 564/397; 564/398

(58) Field of Classification Search ............... None
See application file for complete search history.

(56) References Cited

U.S. PATENT DOCUMENTS

| | | | |
|---|---|---|---|
| 5,350,749 A | 9/1994 | Hackler et al. | |
| 5,688,938 A | 11/1997 | Brown et al. | |
| 5,763,569 A | 6/1998 | Brown et al. | |
| 5,858,684 A | 1/1999 | Nemeth et al. | |
| 5,962,314 A | 10/1999 | Brown et al. | |
| 5,981,599 A | 11/1999 | Moe et al. | |
| 6,001,884 A | 12/1999 | Nemeth et al. | |
| 6,011,068 A | 1/2000 | Nemeth et al. | |
| 6,031,003 A | 2/2000 | Nemeth et al. | |
| 6,211,244 B1 | 4/2001 | Van Wagenen et al. | |
| 6,313,146 B1 | 11/2001 | Van Wagenen et al. | |
| 6,342,532 B1 | 1/2002 | Moe et al. | |
| 6,362,231 B1 | 3/2002 | Sakai et al. | |
| 6,710,088 B2 | 3/2004 | Moe et al. | |
| 6,750,255 B2 | 6/2004 | Sakai et al. | |
| 6,908,935 B2 | 6/2005 | Kelly et al. | |
| 6,939,895 B2 | 9/2005 | Sakai et al. | |
| 2003/0176485 A1 | 9/2003 | Sakai et al. | |
| 2004/0077619 A1 | 4/2004 | Kelly et al. | |
| 2004/0082625 A1 | 4/2004 | Kelly et al. | |
| 2005/0143426 A1 | 6/2005 | Kelly et al. | |
| 2005/0192317 A1 | 9/2005 | Dauban et al. | |

FOREIGN PATENT DOCUMENTS

| | | |
|---|---|---|
| DE | 4037960 A1 | 6/1992 |
| WO | WO93/04373 | 3/1993 |
| WO | WO94/18959 | 9/1994 |
| WO | WO95/11221 | 4/1995 |
| WO | WO96/12697 | 5/1996 |
| WO | WO97/41090 | 11/1997 |
| WO | WO98/01417 | 1/1998 |
| WO | WO01/34562 | 5/2001 |
| WO | WO01/90069 | 11/2001 |
| WO | WO02/02505 | 1/2002 |
| WO | WO02/02512 | 1/2002 |
| WO | WO02/02518 | 1/2002 |
| WO | WO02/12181 | 2/2002 |
| WO | WO03/099776 | 12/2003 |
| WO | WO03/099814 | 12/2003 |
| WO | WO2004/017908 | 3/2004 |
| WO | WO2005/115975 | 12/2005 |

OTHER PUBLICATIONS

Berge, Stephen M., et al., "Pharmaceutical Salts," *Journal of Pharmaceutical Sciences*, vol. 66, No. 1, pp. 1-19, Jan. 1977.
Duquette, Jason, et al., "A Scalable Asymmetric Synthesis of (R)-2-Amino-1-(3-pyridinyl)ethanol Dihydrochloride via an Oxazaborolidine Catalyzed Borane Reduction," *Organic Process Research & Development*, vol. 7, No. 3, pp. 285-288 (2003).
Franceschini, Nora, et al., "Cinacalcet HCl: A Calcimimetic Agent for the Management of Primary and Secondary Hyperparathyroidism," *Expert Opin. Investig. Drugs*, vol. 12, No. 8, pp. 1413-1421 (2003).
Pendrak, Israil and Chambers, Pamela A., "Improved Synthesis of RG-14893, a High-Affinity Leukotriene $B_4$ Receptor Antagonist, via a Photochemical Wolff Rearrangement," *J. Org. Chem.*, vol. 60, pp. 3249-3251 (1995).
Thompson, Andrew S., et al., "Direct Conversion of Activated Alcohols to Azides Using Diphenyl Phosphorazidate. A Practical Alternative to Mitsunobu Conditions," *J. Org. Chem.*, vol. 58, pp. 5886-5888 (1993).
Vogl, Erasmus M. and Buchwald, Stephen L., "Palladium-Catalyzed Monoarylation of Nitroalkanes," *J. Org. Chem.*, vol. 67, pp. 106-111 (2002).
Wang, Xin, et al., "Synthesis of Cinacalcet Congeners," *Tetrahedron Letters*, vol. 45, pp. 8355-8358 (2004).
Chen, Ying, "ORGN 497 Synthesis of Cinacalcet Congeners," Abstract from Proceedings of 228th American Chemical Society Meeting in Philadelphia (2004).

*Primary Examiner*—Brian Davis
(74) *Attorney, Agent, or Firm*—Olga Mekhovich

(57) ABSTRACT

The present invention relates to novel dihydronaphthalene compounds, compositions, methods for using the same, and processes for preparing the same. The present invention also relates to novel total synthesis approaches for preparing these compounds. In addition, the present invention relates to methods of producing quantities of isomers of these compounds and separating and purifying them using chiral separation techniques. The present invention also relates to methods of producing quantities of a single isometric compound without the need for chiral separation techniques.

48 Claims, 1 Drawing Sheet

DIHYDRONAPHTHALENE COMPOUNDS, COMPOSITIONS, USES THEREOF, AND METHODS FOR SYNTHESIS

CROSS-REFERENCE TO RELATED APPLICATIONS

This application claims the benefit of United States Provisional Application No. 60/591,624 filed Jul. 28, 2004, which is incorporated herein by reference in its entirety.

BACKGROUND OF THE INVENTION

Calcium receptor-active compounds are known in the art. One example of a calcium receptor-active compound is cinacalcet HCl, which is described, for example, in U.S. Pat. No. 6,001,884, and has the following structure:

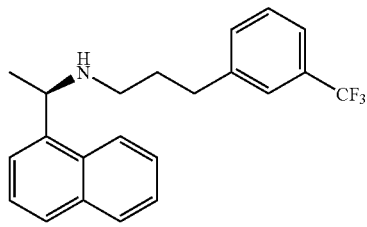

Such calcium receptor-active compounds may be insoluble or sparingly soluble in water, particularly in their non-ionized state. For example, cinacalcet has a solubility in water of less than about 1 μg/mL at neutral pH. The solubility of cinacalcet can reach about 1.6 mg/mL when the pH ranges from about 3 to about 5. However, when the pH is about 1, the solubility decreases to about 0.1 mg/mL. Such limited solubility can reduce the number of formulation and delivery options available for these calcium receptor-active compounds. Limited water solubility can also result in low bioavailability of the compounds.

SUMMARY OF THE INVENTION

It has been discovered that low levels (<0.1%) of two new calcium receptor-active isometric dihydronaphthalenes 1 and 2 can be formed during the manufacture of cinacalcet.

Scheme 1

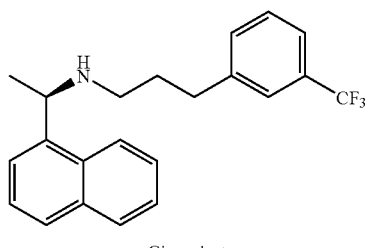

Cinacalcet

-continued

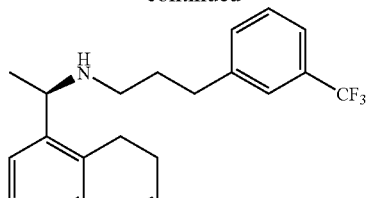

1

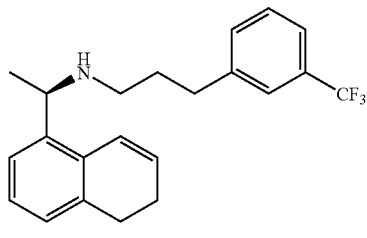

2

Embodiments of the present invention provide methods of synthesizing isomeric dihydronaphthalenes. Certain embodiments of the present invention are directed to methods of synthesizing isomers of cinacalcet.

Certain embodiments of the present invention provide compounds, compositions, and uses comprising dihydronaphthalene compounds. Embodiments of the present invention also provide methods of synthesizing dihydronaphthalene compounds. Embodiments of the present invention also provide methods of synthesizing isomeric dihydronaphthalenes, which results in a composition comprising two different isomers. In some embodiments of the invention these two isomers are dihydronaphthalene compounds 1 and 2, or synthetic intermediates thereof. According to certain embodiments of the invention, chiral HPLC chromatography may be used to achieve high yields of an individual isomer when more than one isomer is present.

Embodiments of the invention also provide methods of synthesizing isomeric dihydronaphthalenes, which results in a composition comprising only a single isomer. According to certain embodiments of the invention, methods of synthesizing isomeric dihydronaphthalenes are provided which do not require use of chiral HPLC chromatography to achieve high yields of an individual isomer.

In some embodiments of the present invention, the compounds produced by the synthetic methods of the present invention may be therapeutically effective for the treatment of hyperparathyroidism, such as primary hyperparathyroidism and secondary hyperparathyroidism, hyperphosphonia, hypercalcemia, and elevated calcium phosphorus product.

One embodiment of the invention relates to a compound chosen from

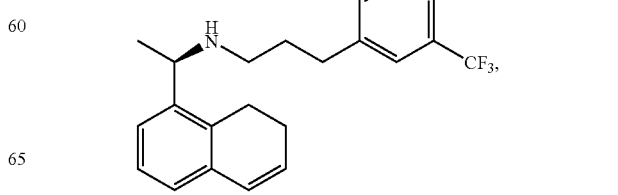

(1)

-continued (2)

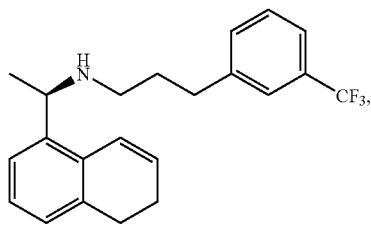

optionally substituted derivatives thereof, isomers thereof, solvates thereof, or salts thereof.

Another embodiment of the present invention relates to a composition (1)

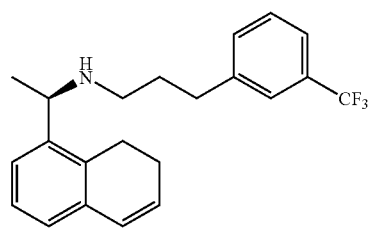

(2)

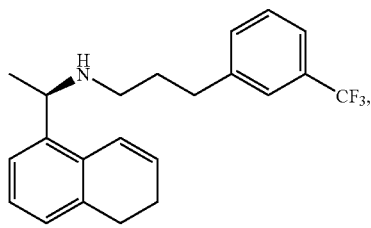

optionally substituted derivatives thereof, isomers thereof, solvates thereof, or salts thereof;

and at least one acceptable carrier.

The present invention also relates to a process for the preparation of at least one dihydronaphthalene compound wherein the process comprises reacting at least one compound A with at least one compound B, wherein compound A is chosen from (9a)

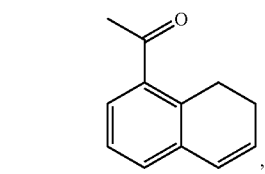

-continued (9b)

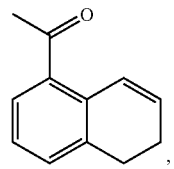

optionally substituted derivatives thereof, isomers thereof, solvates thereof, salts thereof, and mixtures thereof; and compound B is chosen from (13)

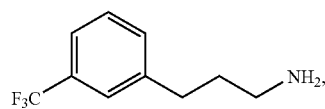

optionally substituted derivatives thereof, isomers thereof, solvates thereof, salts thereof, and mixtures thereof, wherein compounds A and B react to form a dihydronaphthalene compound. The present invention may include the above process, wherein the at least one dihydronaphthalene compound formed is (1)

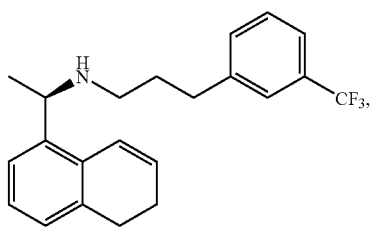

(2)

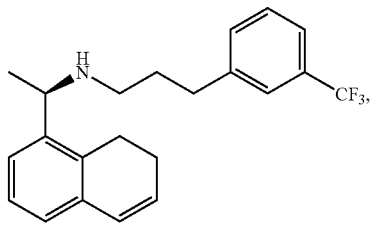

or mixtures thereof.

The present invention may includes at least one of the above processes, wherein the process comprises forming compound A from

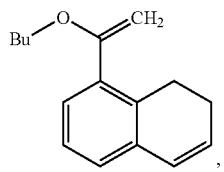

8a

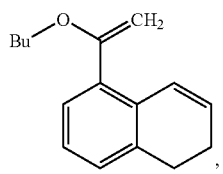

8b isomers thereof, optionally substituted derivatives thereof, or mixtures thereof.

The present invention may include at least one of the above processes, wherein compound A is formed by reacting

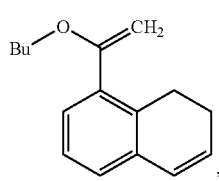

8a

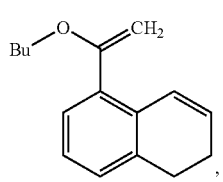

8b isomers thereof, optionally substituted derivatives thereof, or mixtures thereof with an acid.

The present invention may include the above process, wherein the acid is HCl.

The present invention may include at least one of the above processes, wherein

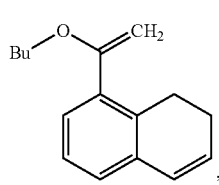

8a

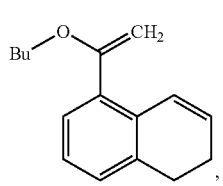

8b isomers thereof, optionally substituted derivatives thereof, or mixtures thereof are formed by reacting at least one compound C with at least one compound D, wherein C is chosen from

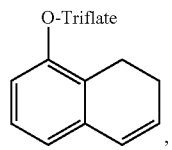

isomers thereof, and optionally substituted derivatives thereof; and compound D is chosen from

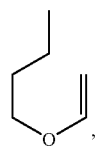

isomers thereof, and optionally substituted derivatives thereof.

The present invention may include the above process, wherein at least one compound C is reacted with at least one compound D in the presence of a catalyst.

The present invention may include the above process, wherein at least one compound C is reacted with at least one compound D in the presence of a catalyst comprising palladium.

The present invention may include at least one of the above processes, wherein at least one of

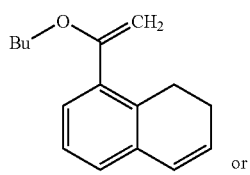

8a or

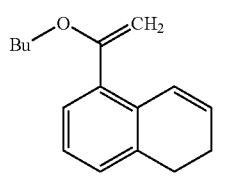

8b is formed as an intermediate.

The present invention may include at least one of the above processes, wherein

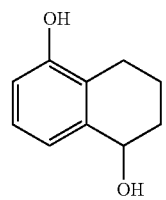

is reacted with triflate anhydride and tetraethylamine in dichloromethane to form

  5

The present invention may include at least one of the above processes, wherein

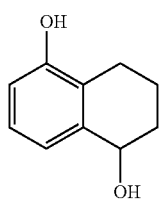

is formed from

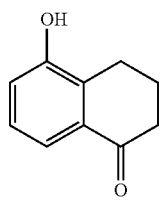

The present invention may include at least one of the above processes wherein

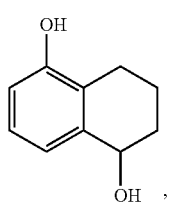

is reacted with NaBH$_4$ and MeOH to form

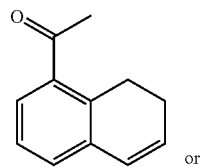

The present invention may include at least one of above processes, wherein at least one of

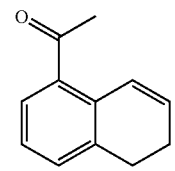

is formed.

The present invention may include at least one of the above processes, wherein

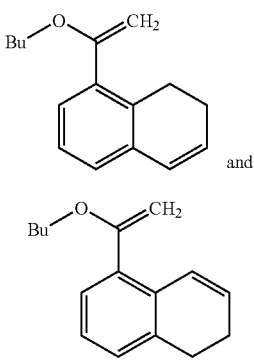

are formed at an 8a:8b weight ratio ranging from 10:1 to 1:2.

The present invention may include the above process, wherein compounds 8a and 8b are formed at a 8a:8b weight ratio ranging from 9:1 to 1:1.

The present invention may include the above process, wherein compounds 8a and 8b are formed at a 8a:8b weight ratio ranging from 3:1 to 1.5:1.

The present invention may include at least one of the above processes, wherein compounds 9a and 9b are separated and purified using chromatography.

The present invention may include at least one of the above processes, wherein compound 9a and 9b are separated and purified using chiral HPLC.

The present invention may include at least one of the above processes, wherein compound 1, compound 2, or mixtures thereof are separated and purified using chromatography.

The present invention may include at least one of the above processes, wherein compound 1 and compound 2 are separated and purified using chiral HPLC.

The present invention may include at least one of the above processes, wherein

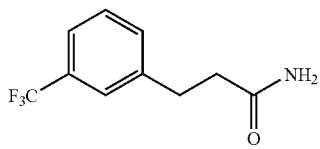

is reduced with lithium aluminum hydride to form

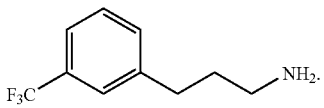

The present invention may include the above process, wherein

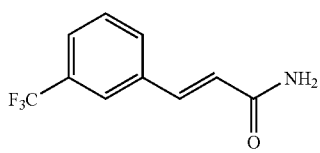

is reduced by hydrogenation to form

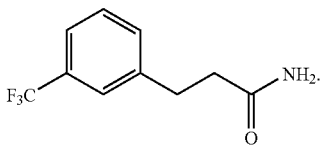

The present invention may include the above process, wherein

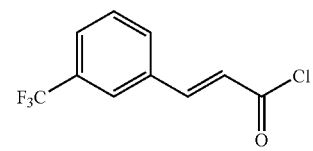

is reacted with NH$_4$OH to form

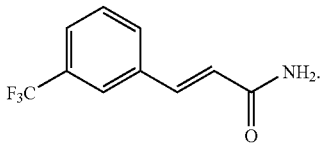

One embodiment of the present invention relates to a process for the preparation of at least one dihydronaphthalene compound wherein the process comprises reacting at least one compound E with at least one compound G, wherein compound E is chosen from

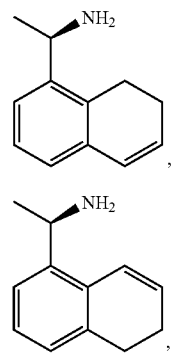

isomers thereof, and optionally substituted derivatives thereof; and
compound G is chosen from

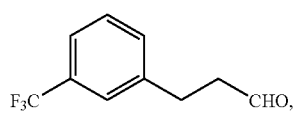

isomers thereof, and optionally substituted derivatives thereof,
wherein compounds E and G react to form a dihydronaphthalene compound.

The present invention may include the above process, wherein the at least one dihydronaphthalene compound formed is

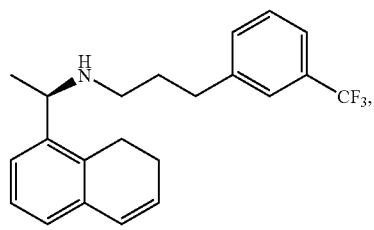

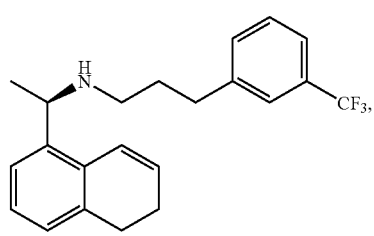

or mixtures thereof.

The present invention may include at least one of the above processes, wherein the process comprises forming compound E from

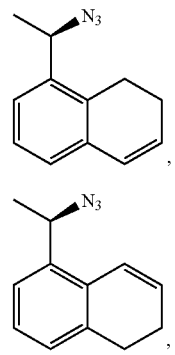

18a

18b isomers thereof, optionally substituted derivatives thereof, or mixtures thereof.

The present invention may include the above process, wherein compound E is formed by reducing

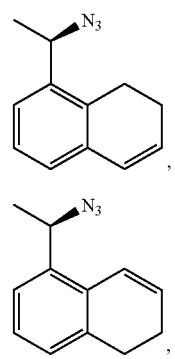

18a

18b isomers thereof, optionally substituted derivatives thereof, or mixtures thereof in the presence of Ph$_3$P.

The present invention may include the above process, wherein

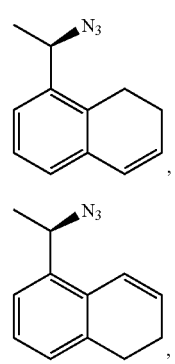

18a

18b isomers thereof, optionally substituted derivatives thereof, or mixtures thereof are formed by converting

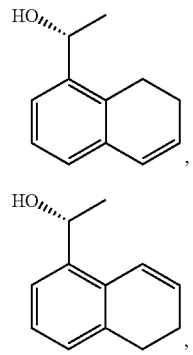

17a

17b isomers thereof, optionally substituted derivatives thereof, or mixtures thereof to an azide using (PhO)$_2$PON$_3$.

The present invention may include the above process, wherein

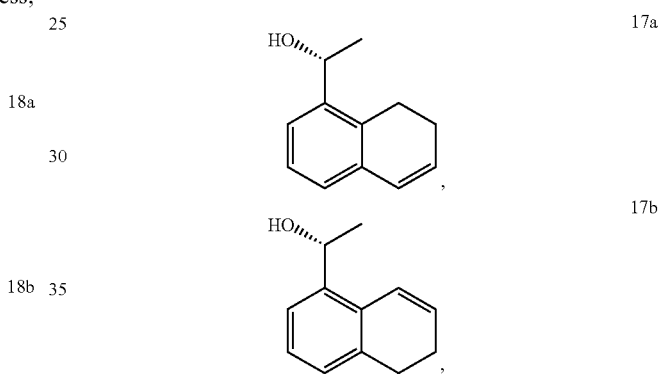

17a

17b isomers thereof, optionally substituted derivatives thereof, or mixtures thereof are formed by reducing

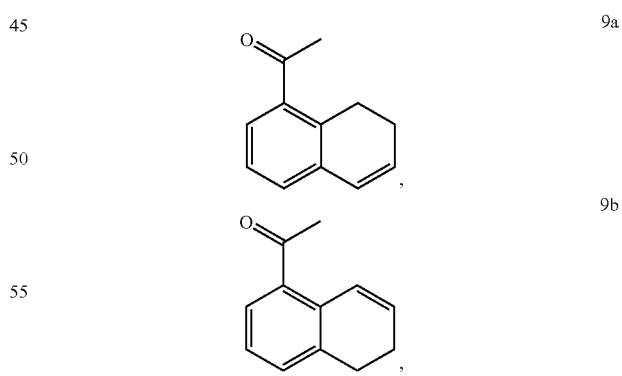

9a

9b isomers thereof, optionally substituted derivatives thereof, or mixtures thereof to an alcohol using a borane reduction.

The present invention may include the above process, wherein the borane reduction is catalyzed by methyl oxazaborolidine.

The present invention may include at least one of the above processes, wherein

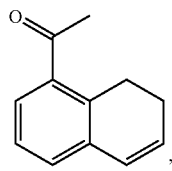

isomers thereof, or optionally substituted derivatives thereof, or mixtures thereof are formed by reacting

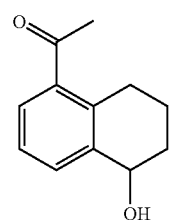

with triflate anhydride and tetraethylamine in dichloromethane followed by elimination of the hydroxyl group.

The present invention may include the above process, wherein

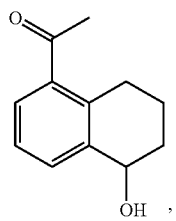

isomers thereof, or optionally substituted derivatives thereof, or mixtures thereof are formed by reacting

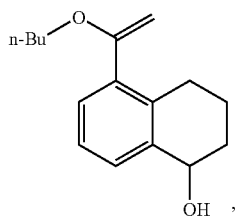

isomers thereof, optionally substituted derivatives thereof, or mixtures thereof with an acid.

The present invention may include the above process, wherein the acid is HCl.

The present invention may include at least one of the above processes, wherein

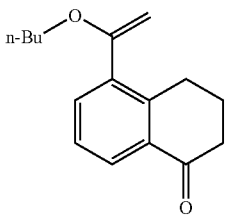

is reacted with NaBH$_4$ and MeOH to form

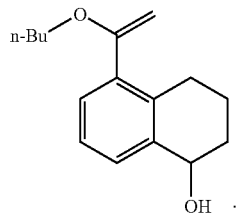

The present invention may include the above process, wherein

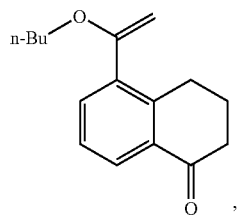

isomers thereof, optionally substituted derivatives thereof, or mixtures thereof are formed by reacting

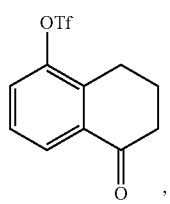

isomers thereof, and optionally substituted derivatives thereof, with

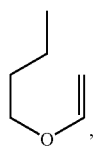

isomers thereof, and optionally substituted derivatives thereof.

The present invention may include the above process, wherein the contact with

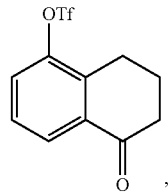 4 isomers thereof, and optionally substituted derivatives thereof, is in the presence of a catalyst.

The present invention may include the above process, wherein the catalyst comprises palladium.

The present invention may include at least one of the above processes, wherein

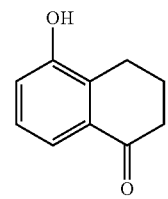 3 is reacted with triflate anhydride and tetraethylamine in dichloromethane to form

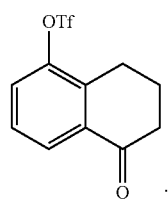 4

The present invention may include at least one of the above processes, wherein

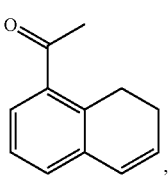 9a

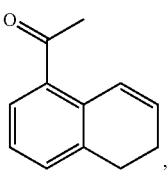 9b isomers thereof, optionally substituted derivatives thereof, or mixtures thereof are formed by reacting

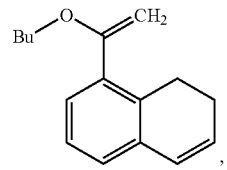 8a

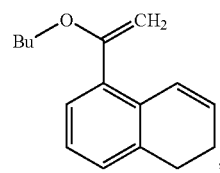 8b isomers thereof, optionally substituted derivatives thereof, or mixtures thereof with an acid.

The present invention may include the above process, wherein the acid is HCl.

The present invention may include at least one of the above processes, wherein

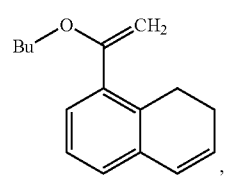 8a

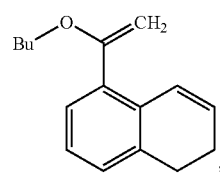 8b isomers thereof, optionally substituted derivatives thereof, or mixtures thereof are formed by reacting at least one compound C with at least one compound D, wherein
    compound C is chosen from

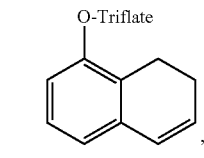

isomers thereof, and optionally substituted derivatives thereof; and
    compound D is chosen from

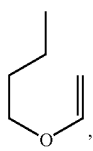, isomers thereof, and optionally substituted derivatives thereof.

The present invention may include the above process, wherein the at least one compound C reacts with at least one compound D in the presence of a catalyst.

The present invention may include the above process, wherein at least one compound C reacts with at least one compound D in the presence of a catalyst comprising palladium.

The present invention may include at least one of the above processes, wherein

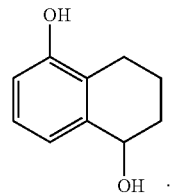

is reacted with triflate anhydride and tetraethylamine in dichloromethane to form

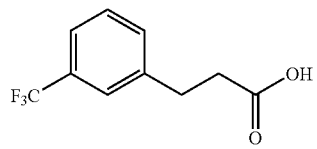

The present invention may include the above process, wherein

is reacted with NaBH₄ and MeOH to form

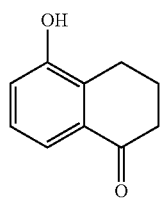

The present invention may include at least one of the above processes, wherein

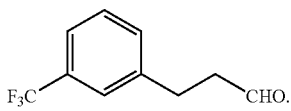

is reduced to form

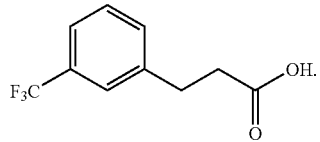

The present invention may include the above process, wherein

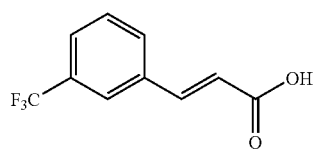

is reduced by hydrogenation to form

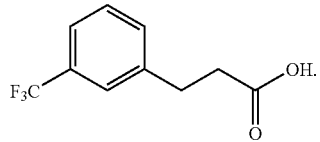

The present invention may include at least one of the above processes, wherein only one of compound 1 or compound 2 is formed.

The present invention may include at least one of the above processes, wherein compound 1, compound 2, or mixtures thereof are purified without the use of chiral HPLC.

One embodiment of the present invention relates to a process for the preparation of a dihydronaphthalene compound wherein the process comprises reacting at least one compound E with at least one compound G,
wherein
compound E is chosen from 19a 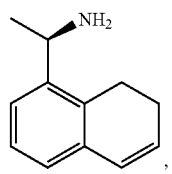, 19b 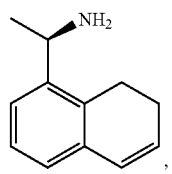, optionally substituted derivatives thereof, isomers thereof, solvates thereof, and salts thereof; and compound G is chosen from 22 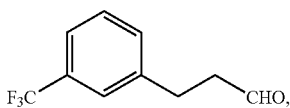, optionally substituted derivatives thereof, isomers thereof, solvates thereof, and salts thereof, wherein compounds E and G react to form a dihydronaphthalene compound;

and wherein the process comprises production of either

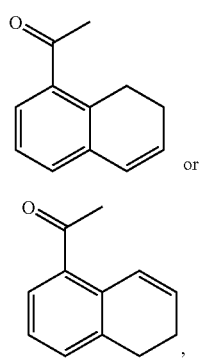

but not mixtures comprising both 9a and 9b.

Another embodiment of the present invention relates to a process for the preparation of

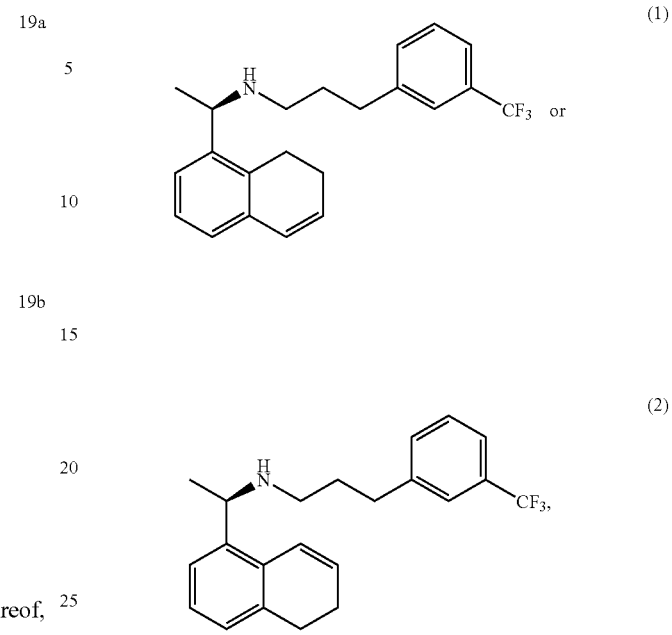

wherein the process does not require the use of chiral chromatography to separate or purify (1) or (2).

DETAILED DESCRIPTION

Figure 1:
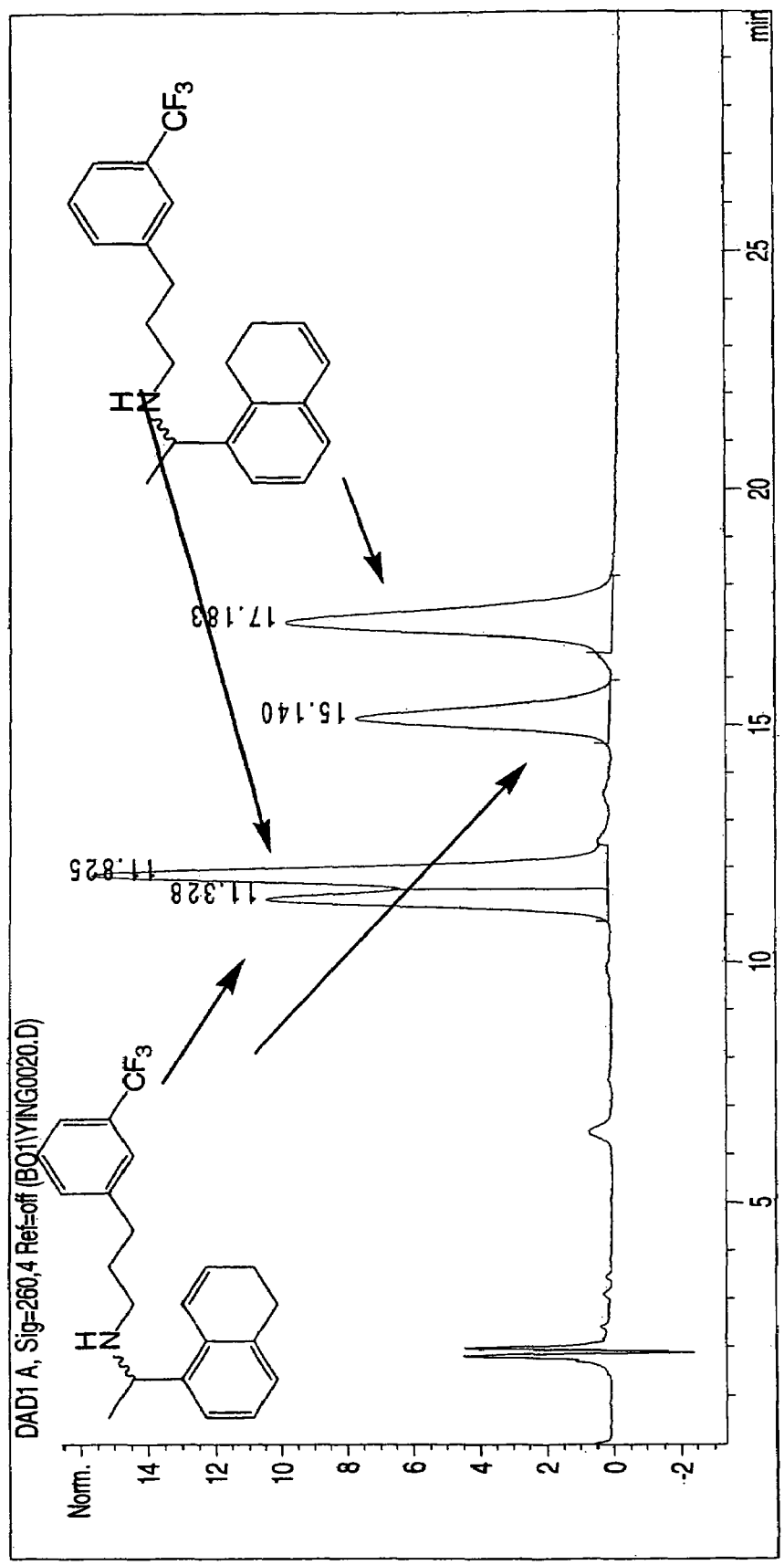
FIG. 1 shows an exemplary HPLC graph of the separation of compounds 1 and 2 using chiral HPLC.

The isomers of the calcium receptor-active compounds synthesized in the claimed invention may be calcimimetic compounds. As used herein, the term "calcimimetic compounds" refers to compounds that bind to a calcium receptor, and include a conformational change that reduces the threshold for calcium receptor activation by the endogenous ligand $Ca^{2+}$, thereby reducing parathyroid hormone ("PTH") secretion. These calcimimetic compounds can also be considered allosteric modulators of the calcium receptor.

Embodiments of compounds of formula (I) of the present invention may encompass all chemically acceptable salts thereof, isomers thereof, solvates thereof such as for example hydrates, and also derivatives of compounds of formula I such as, for example, esters, prodrugs, and active metabolites.

The "salt" may be any as long as it forms at least one salt with a compound of the above-mentioned compounds 1 or 2, or with any synthetic intermediates thereof. The salts may also include "pharmaceutically acceptable salts". The pharmaceutically acceptable salt may be any as long as it forms a non-toxic salt with a compound of the above-mentioned compounds 1 or 2, or with any synthetic intermediates thereof. Salts of the present invention can be obtained by any of the standard methods known to one of skill in the art. For example, a salt of the present invention may be formed by reacting a compound with an inorganic acid such as hydrochloric acid, sulfuric acid, phosphoric acid, hydrobromic acid and the like; or an organic acid such as oxalic acid, malonic acid, citric acid, fumaric acid, lactic acid, malic acid, succinic acid, tartaric acid, acetic acid, trifluoroacetic acid, gluconic acid, ascorbic acid, methylsulfonic acid, benzylsulfonic acid and the like; or an inorganic base such as sodium hydroxide, potassium hydroxide, calcium hydroxide, magnesium hydroxide, ammonium hydroxide and the like; or an organic base such as methylamine, diethylamine, triethylamine, triethanolamine, ethylenediamine, tris(hydroxymethyl)methylamine, guanidine, choline, cinchonine N-methyl-D-glucamine and the like; or an amino acid such as lysine, histidine, arginine, alanine and the like.

The calcium receptor-active compounds synthesized in the claimed invention and their salts may exist in the form of solvates, for example hydrates, and the present invention includes each solvate and mixtures thereof, in solid or liquid state. As used herein, "solvate" means solvent addition forms that contain either stoichiometric or non stoichiometric amounts of solvent. Some compounds have a tendency to trap a fixed molar ratio of solvent molecules in the crystalline solid state, thus forming a solvate. If the solvent is water the solvate formed is a hydrate; when the solvent is alcohol, the solvate formed is an alcoholate. Hydrates are formed by the combination of one or more molecules of water with one of the substances in which the water retains its molecular state as H2O, such combination being able to form one or more hydrate. Examples of hydrates include sesquihydrates, monohydrates, hemihydrates, dihydrates and trihydrates. Also suitable are the hydrates or solvates of salts of the compounds according to the invention, and mixtures thereof.

Dihydronaphthalene compounds made by the methods of the present invention may be isomers of one another. The term "isomer" as used in this specification may refer to, for example, optical isomers, enantiomers, diastereomers, tautomers, conformational isomers, and positional isomers. Embodiments of the present invention may include synthesis of at least one of these isomers and mixtures thereof, and/or use of at least one of these isomers as a synthetic intermediate.

The compounds synthesized by the present inventive method, and their synthetic intermediates, may have various isomers. For example, an E compound and a Z compound are present as geometric isomers, and when the compound has an asymmetric carbon, an enantiomer and a diastereomer are present due to the asymmetric carbon. Certain compounds formed by the presently disclosed synthetic methods may contain one or more chiral centers, and may exist in different optically active forms. In some embodiments, when a compound formed by the presently disclosed inventive synthetic method contains one chiral center, the compound may exist in two enantiomeric forms and the present invention includes both enantiomers and mixtures of enantiomers. The enantiomers may be resolved by methods known to those skill in the art, for example: (i) by formation of diastereoisomeric salts which may be separated, for example, by crystallization; (ii) by formation of diastereoisomeric derivatives or complexes which may be separated, for example, by crystallization, gas-liquid or liquid chromatography; (iii) by selective reaction of one enantiomer with an enantiomer-specific reagent, for example enzymatic esterification; or (iv) by gas-liquid or liquid chromatography in a chiral environment, for example on a chiral support for example silica with a bound chiral ligand or in the presence of a chiral solvent. If the desired enantiomer is converted into another chemical entity by one of the separation procedures described above, a further step is required to liberate the desired enantiomeric form. Such methods are known to those skilled in the art. Alternatively, specific enantiomers may be synthesized by asymmetric synthesis using optically active reagents, substrates, catalysts or solvents, or by converting one enantiomer into the other by asymmetric transformation.

When a compound produced by synthetic methods disclosed herein contains more than one chiral center it may exist in diastereoisomeric forms. The diastereoisomeric pairs may be separated by methods known to those skilled in the art, for example chromatography or crystallization and the individual enantiomers within each pair may be separated as described above. Embodiments of the present invention may include synthesis of at least one diastereoisomer, and/or use of at least one diastereoisomer as a synthetic intermediate.

Certain compounds produced by the synthetic methods disclosed herein may exist in different stable conformational forms that may be separable. Torsional asymmetry due to restricted rotation about an asymmetric single bond, for example because of steric hindrance or ring strain, may permit separation of different conformers. In certain embodiments, the present invention may include synthesis of at least one conformational isomers, and/or use of at least one conformational isomer as a synthetic intermediate. Certain compounds encompassed by the present inventive synthetic methods may exist in zwitterionic form and the present invention may include synthesis of at least one zwitterionic form, and/or use of at least one zwitterionic form as a synthetic intermediate.

"Substituted", as used herein, refers to a group in which one or more hydrogen atoms are each independently replaced with the same or different substituent(s). Typical substituents include but are not limited to CH3, CH3O, CH3CH2O, methylene dioxy, Br, Cl, F, I. CF3, CHF2, CH2F, CF3O, CF3CH2O, CH3S, OH, CH2OH, CONH2, CN, NO2, CH3CH2, propyl, isopropyl, butyl, isobutyl, t-butyl, and acetoxy. The term "substituted derivative" refers to a subject compound or isomer thereof in which one or more hydrogen atoms are each independently replaced with the same or different substituent(s). For example, an optionally substituted derivative of compound 1 or 2 would be a compound 1 or 2 wherein at least one appropriate hydrogen, for example, a hydrogen on one of the ring structures, of compound 1 or 2 is optionally replaced with one of the above defined substituents.

Calcium receptor-active compounds synthesized using the methods of the present invention can be further derivatized to form pharmaceutically acceptable salts derived from inorganic or organic acids. The salts include, but are not limited to, the following: acetate, adipate, alginate, citrate, aspartate, benzoate, benzenesulfonate, bisulfate, butyrate, camphorate, camphorsulfonate, digluconate, cyclopentanepropionate, dodecylsulfate, ethanesulfonate, glucoheptanoate, glycerophosphate, hemisulfate, heptanoate, hexanoate, fumarate, hydrochloride, hydrobromide, hydroiodide, 2-hydroxy-ethanesulfonate, lactate, maleate, mandelate, methansulfonate, nicotinate, 2-naphthalenesulfonate, oxalate, palmoate, pectinate, persulfate, 2-phenylpropionate, picrate, pivalate, propionate, salicylate, succinate, sulfate, tartrate, thiocyanate, tosylate, mesylate, and undecanoate. When compounds of the invention include an acidic function such as a carboxy group, then suitable pharmaceutically acceptable salts for the carboxy group are well known to those skilled in the art and include, for example, alkaline, alkaline earth, ammonium, quaternary ammonium cations and the like. For additional examples of "pharmacologically acceptable salts," see infra and Berge et al., J. Pharm. Sci. 66:1 (1977). In certain embodiments of the invention salts of hydrochloride and salts of methanesulfonic acid can be used.

In some embodiments of the present invention, the synthesized calcium-receptor active compounds can be in various forms, such as amorphous powders, crystalline powders, and mixtures thereof. For example, the crystalline powders can be in forms including polymorphs, pseudopolymorphs, crystal habits, micromeretics, and particle morphology. The inventive compounds may also be provided as compositions comprising a suitable acceptable carrier. Acceptable carriers as used in this invention may include pharmaceutically acceptable carriers and suitable solvents including solvents known to be useful by one of skill in the art for solubilizing small molecules, for example, water, aqueous buffers, organic solvents, and inorganic solvents.

In addition, when the inventive compound is used as a pharmaceutical preparation, the inventive compound is generally admixed with pharmaceutically acceptable carriers, excipients, diluents, fillers, disintegrators, stabilizers, preservatives, buffers, emulsifiers, aromatics, coloring agents, sweeteners, thickeners, correctives, solubilizers, and other additives such as water, vegetable oil, alcohol such as ethanol, benzyl alcohol and the like, polyethylene glycol, glycerol triacetate, gelatin, lactose, carbohydrate such as starch and the like, magnesium stearate, talc, lanolin, petrolatum and the like, and prepared into a dosage form, for example, of tablets, pills, powders, granules, suppositories, injections, eye drops, liquids, capsules, troches, aerosols, elixirs, suspensions, emulsions, syrups and the like, which can be administered systemically or topically and orally or parenterally.

In some embodiments of the present invention, the compounds produced by the synthetic methods of the present invention may be therapeutically effective for the treatment of hyperparathyroidism, such as primary hyperparathyroidism and secondary hyperparathyroidism, hyperphosphonia, hypercalcemia, and elevated calcium-phosphorus product.

One embodiment of the invention relates to a compound chosen from

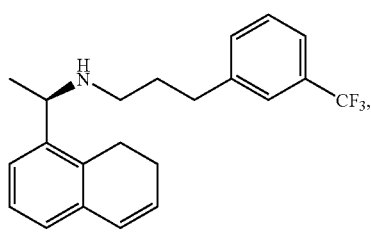
(1)

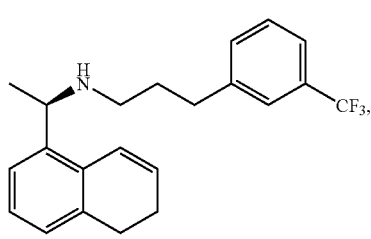
(2)

optionally substituted derivatives thereof, isomers thereof, solvates thereof, or salts thereof.

Another embodiment of the present invention relates to a composition comprising at least one compound chosen from

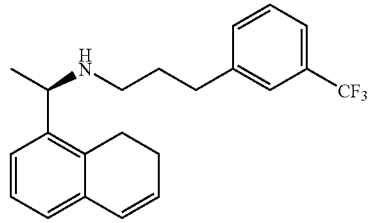
(1)

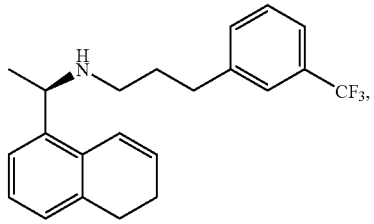
(2)

optionally substituted derivatives thereof, isomers thereof, solvates thereof, or salts thereof;
and at least one acceptable carrier.

The present invention also relates to a process for the preparation of at least one dihydronaphthalene compound wherein the process comprises reacting at least one compound A with at least one compound B, wherein compound A is chosen from

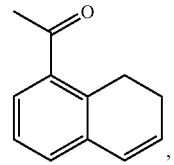
(9a)

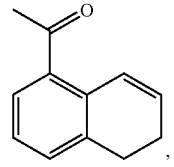
(9b)

optionally substituted derivatives thereof, isomers thereof, solvates thereof, salts thereof, and mixtures thereof; and compound B is chosen from

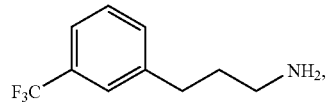
(13)

optionally substituted derivatives thereof, isomers thereof, solvates thereof, salts thereof, and mixtures thereof, wherein compounds A and B react to form a dihydronaphthalene compound.

The present invention may include the above process, wherein the at least one dihydronaphthalene compound formed is (1)

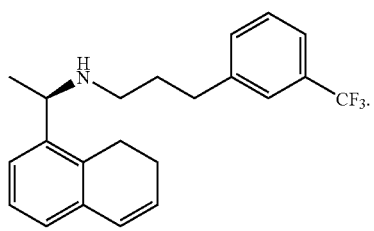

(2)

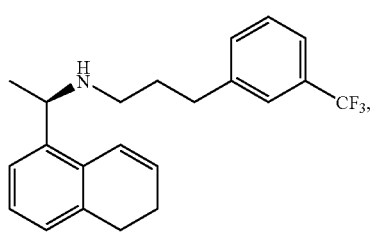

or mixtures thereof.

The present invention may include at least one of the above processes, wherein the process comprises forming compound A from

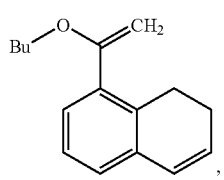
8a

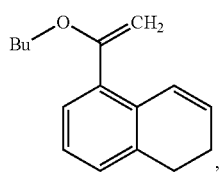
8b isomers thereof, optionally substituted derivatives thereof, or mixtures thereof.

The present invention may include at least one of the above processes, wherein compound A is formed by reacting

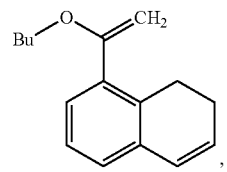
8a

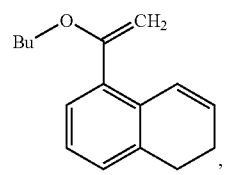
8b isomers thereof, optionally substituted derivatives thereof, or mixtures thereof with an acid.

The present invention may include the above process, wherein the acid is HCl.

The present invention may include at least one of the above processes, wherein

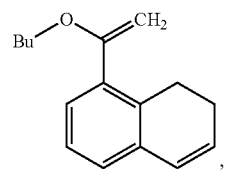
8a

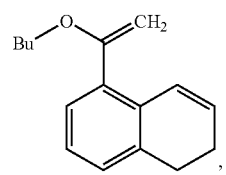
8b isomers thereof, optionally substituted derivatives thereof, or mixtures thereof are formed by reacting at least one compound C with at least one compound D, wherein C is chosen from

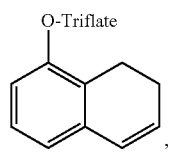

isomers thereof, and optionally substituted derivatives thereof; and compound D is chosen from

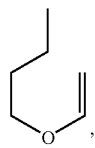

isomers thereof, and optionally substituted derivatives thereof.

The present invention may include the above process, wherein at least one compound C is reacted with at least one compound D in the presence of a catalyst.

The present invention may include the above process, wherein at least one compound C is reacted with at least one compound D in the presence of a catalyst comprising palladium.

The present invention may include at least one of the above processes, wherein at least one of

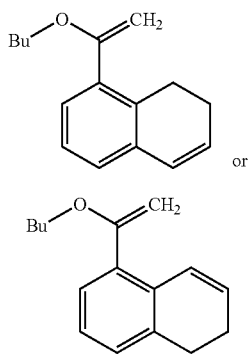

8a or

8b is formed as an intermediate.

The present invention may include at least one of the above processes, wherein

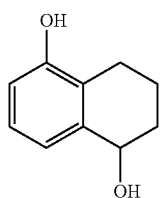

is reacted with triflate anhydride and tetraethylamine in dichloromethane to form

The present invention may include at least one of the above processes, wherein

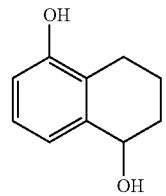

is formed from

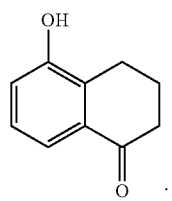

The present invention may include at least one of the above processes wherein

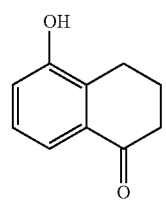

is reacted with NaBH$_4$ and MeOH to form

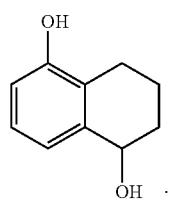

The present invention may include at least one of the above processes, wherein at least one of

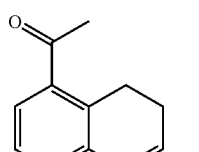

9a or

9b

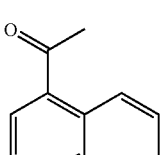

is formed.

The present invention may include at least one of the above processes, wherein

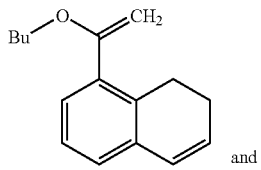 8a and

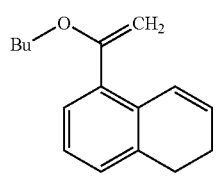 8b are formed at an 8a:8b weight ratio ranging from 10:1 to 1:2.

The present invention may include the above process, wherein compounds 8a and 8b are formed at a 8a:8b weight ratio ranging from 9:1 to 1:1.

The present invention may include the above process, wherein compounds 8a and 8b are formed at a 8a:8b weight ratio ranging from 3:1 to 1.5:1.

The present invention may include at least one of the above processes, wherein compounds 9a and 9b are separated and purified using chromatography.

The present invention may include at least one of the above processes, wherein compound 9a and 9b are separated and purified using chiral HPLC.

The present invention may include at least one of the above processes, wherein compound 1, compound 2, or mixtures thereof are separated and purified using chromatography.

The present invention may include at least one of the above processes, wherein compound 1 and compound 2 are separated and purified using chiral HPLC.

The present invention may include at least one of the above processes, wherein

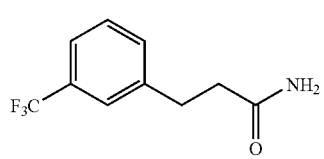 12 is reduced with lithium aluminum hydride to form

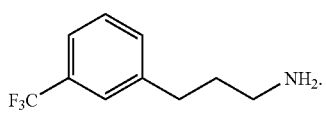 13

The present invention may include the above process, wherein

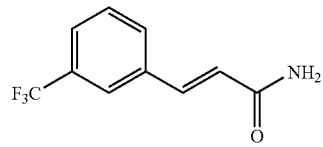 11 is reduced by hydrogenation to form

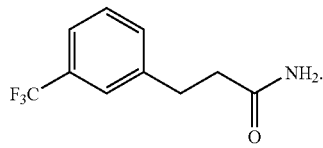 12

The present invention may include the above process, wherein

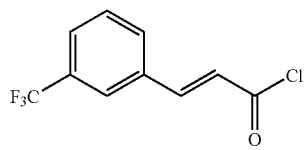 10 is reacted with NH$_4$OH to form

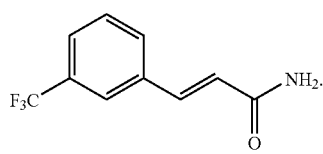 11

One embodiment of the present invention relates to a process for the preparation of at least one dihydronaphthalene compound wherein the process comprises reacting at least one compound E with at least one compound G, wherein compound E is chosen from

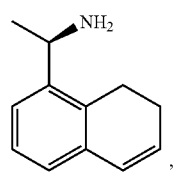 19a

-continued

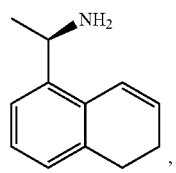

isomers thereof, and optionally substituted derivatives thereof; and compound G is chosen from

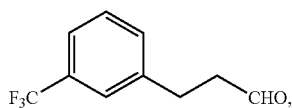

isomers thereof, and optionally substituted derivatives thereof, wherein compounds E and G react to form a dihydronaphthalene compound.

The present invention may include the above process, wherein the at least one dihydronaphthalene compound formed is (1)

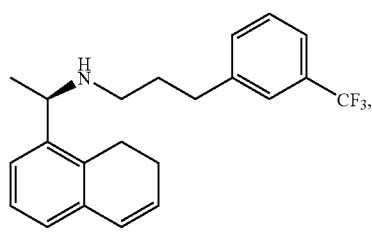

(2)

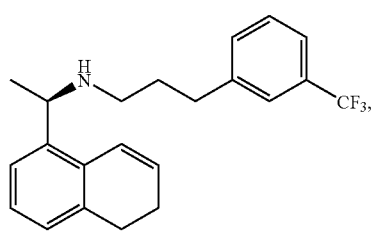

or mixtures thereof.

The present invention may include at least one of the above processes, wherein the process comprises forming compound E from

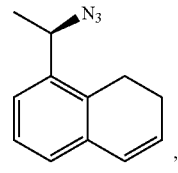

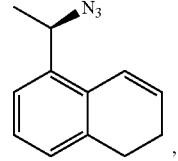

isomers thereof, optionally substituted derivatives thereof, or mixtures thereof.

The present invention may include the above process, wherein compound E is formed by reducing

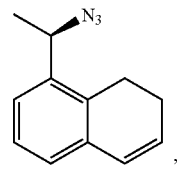

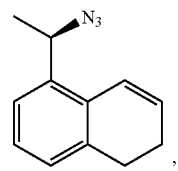

isomers thereof, optionally substituted derivatives thereof, or mixtures thereof in the presence of Ph₃P.

The present invention may include the above process, wherein

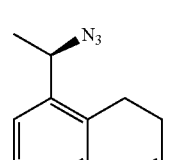

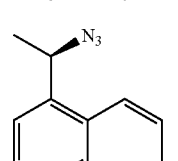

isomers thereof, optionally substituted derivatives thereof, or mixtures thereof are formed by converting

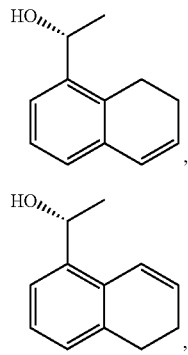

isomers thereof, optionally substituted derivatives thereof, or mixtures thereof to an azide using (PhO)$_2$PON$_3$.

The present invention may include the above process, wherein

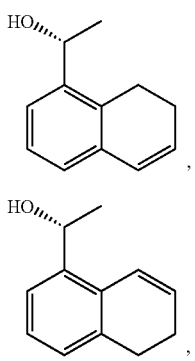

isomers thereof, optionally substituted derivatives thereof, or mixtures thereof are formed by reducing

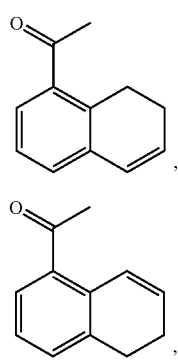

isomers thereof, optionally substituted derivatives thereof, or mixtures thereof to an alcohol using a borane reduction.

The present invention may include the above process, wherein the borane reduction is catalyzed by methyl oxazaborolidine.

The present invention may include at least one of the above processes, wherein

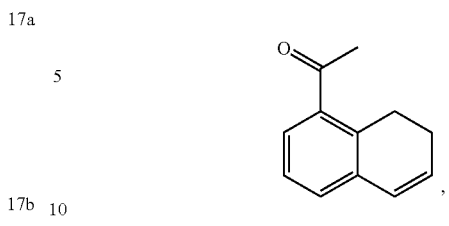

isomers thereof, or optionally substituted derivatives thereof, or mixtures thereof are formed by reacting

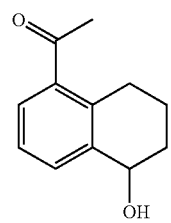

with triflate anhydride and tetraethylamine in dichloromethane followed by elimination of the hydroxyl group.

The present invention may include the above process, wherein

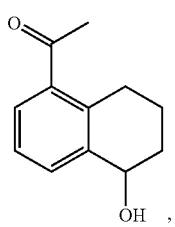

isomers thereof, or optionally substituted derivatives thereof, or mixtures thereof are formed by reacting

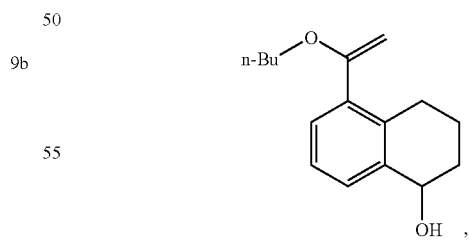

isomers thereof, optionally substituted derivatives thereof, or mixtures thereof with an acid.

The present invention may include the above process, wherein the acid is HCl.

The present invention may include at least one of the above processes, wherein

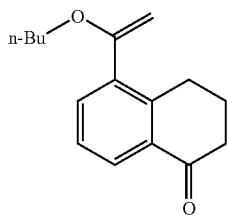

is reacted with NaBH₄ and MeOH to form

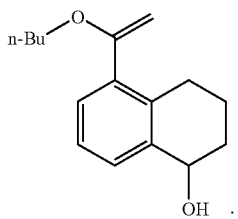

The present invention may include the above process, wherein

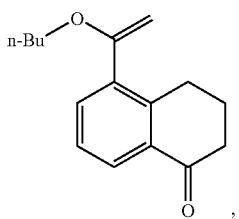

isomers thereof, optionally substituted derivatives thereof, or mixtures thereof are formed by reacting

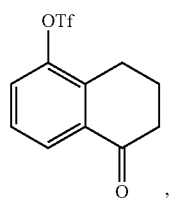

isomers thereof, and optionally substituted derivatives thereof, with

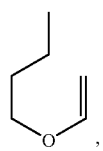

isomers thereof, and optionally substituted derivatives thereof.

The present invention may include the above process, wherein the contact with

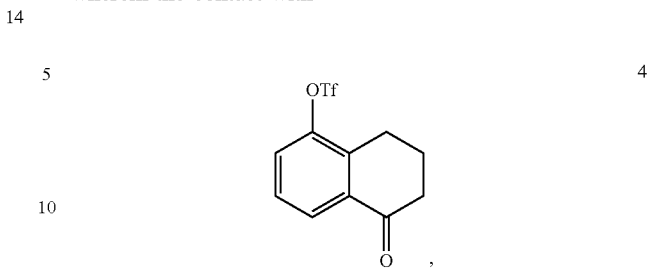

isomers thereof, and optionally substituted derivatives thereof, is in the presence of a catalyst.

The present invention may include the above process, wherein the catalyst comprises palladium.

The present invention may include at least one of the above processes, wherein

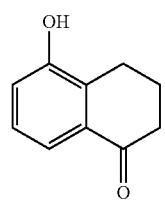

is reacted with triflate anhydride and tetraethylamine in dichloromethane to form

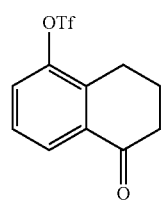

The present invention may include at least one of the above processes, wherein

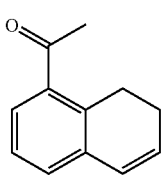

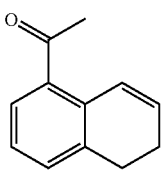

isomers thereof, optionally substituted derivatives thereof, or mixtures thereof are formed by reacting

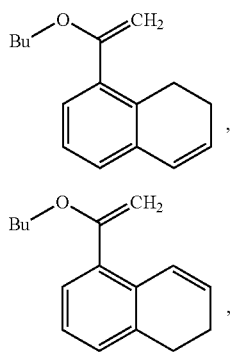

isomers thereof, optionally substituted derivatives thereof, or mixtures thereof with an acid.

The present invention may include the above process, wherein the acid is HCl.

The present invention may include at least one of the above processes, wherein

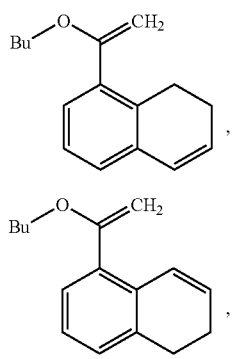

isomers thereof, optionally substituted derivatives thereof, or mixtures thereof are formed by reacting at least one compound C with at least one compound D, wherein
compound C is chosen from

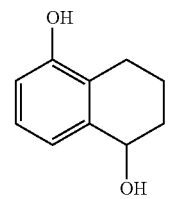

isomers thereof, and optionally substituted derivatives thereof; and
compound D is chosen from

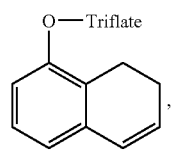

isomers thereof, and optionally substituted derivatives thereof.

The present invention may include the above process, wherein the at least one compound C reacts with at least one compound D in the presence of a catalyst.

The present invention may include the above process, wherein at least one compound C reacts with at least one compound D in the presence of a catalyst comprising palladium.

The present invention may include at least one of the above processes, wherein

is reacted with triflate anhydride and tetraethylamine in dichloromethane to form

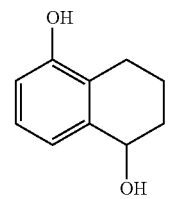

The present invention may include the above process, wherein

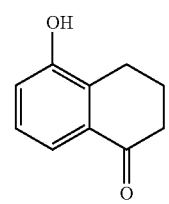

is reacted with NaBH₄ and MeOH to form

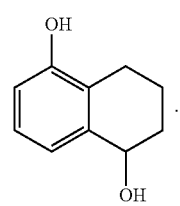

The present invention may include at least one of the above processes, wherein

![compound 21 - 3-(trifluoromethyl)phenyl propanoic acid]

is reduced to form

![compound 22 - 3-(trifluoromethyl)phenyl acetaldehyde derivative, CHO]

The present invention may include the above process, wherein

![compound 20 - 3-(trifluoromethyl)cinnamic acid]

is reduced by hydrogenation to form

![compound 21]

The present invention may include at least one of the above processes, wherein only one of compound 1 or compound 2 is formed.

The present invention may include at least one of the above processes, wherein compound 1, compound 2, or mixtures thereof are purified without the use of chiral HPLC.

One embodiment of the present invention relates to a process for the preparation of a dihydronaphthalene compound wherein the process comprises reacting at least one compound E with at least one compound G, wherein
compound E is chosen from ![compound 19a - (R)-1-(5,6-dihydronaphthalen-1-yl)ethanamine]

![compound 19b - (S)-1-(5,6-dihydronaphthalen-1-yl)ethanamine]

optionally substituted derivatives thereof, isomers thereof, solvates thereof, and salts thereof; and compound G is chosen from ![compound 22]

optionally substituted derivatives thereof, isomers thereof, solvates thereof, and salts thereof, wherein compounds E and G react to form a dihydronaphthalene compound;

and wherein the process comprises production of either

![compound 9a - acetyl dihydronaphthalene]

or

![compound 9b - acetyl dihydronaphthalene]

but not mixtures comprising both 9a and 9b.

Another embodiment of the present invention relates to a process for the preparation of ![compound (1) - N-[1-(5,6-dihydronaphthalen-1-yl)ethyl]-3-(3-(trifluoromethyl)phenyl)propan-1-amine]

or

-continued

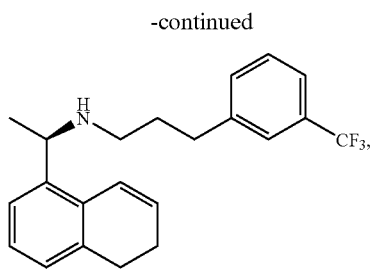

(2)

wherein the process does not require the use of chiral chromatography to separate or purify (1) or (2).

Reference will now be made to the following examples, which are not intended to limit the invention. To the contrary, it will be appreciated that various alternatives, modifications, and equivalents may be included within the spirit and scope of the invention.

EXAMPLES

1. Synthetic Method I: Racemic Synthesis and Chiral Separation

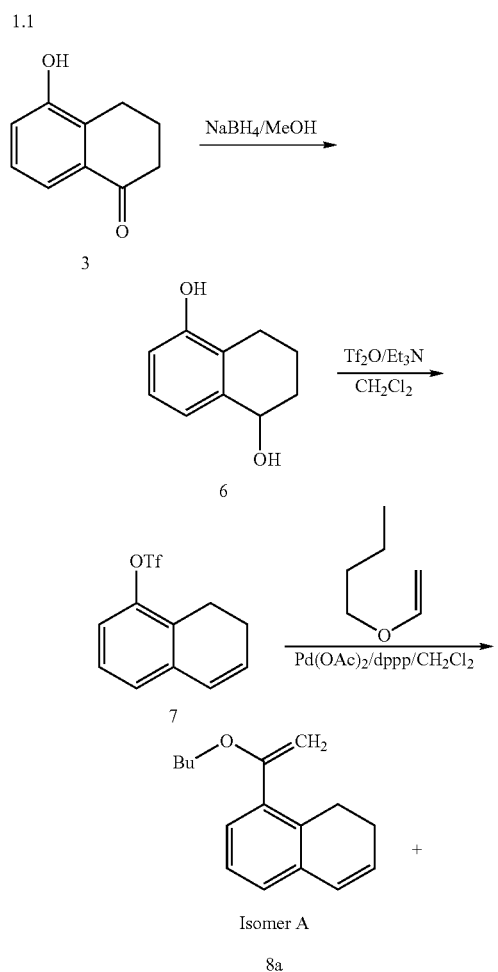

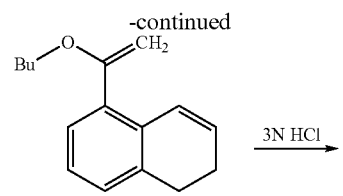

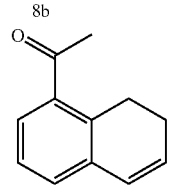 + 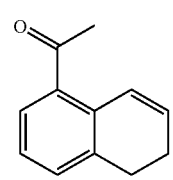

9a          9b

Separated by Chromatography

5-Hydroxytetralone (3) was first reduced with NaBH4 to the alcohol 6. The formation of the triflate group and the elimination step were carried out in one pot using 2 eq. of triflate anhydride and TEA in DCM to give triflate 7. The reactions were clean.

The triflate 7 was converted to a mixture of two isomeric enol vinyl ethers 8 via the Heck coupling reaction. The reaction needed 16 hrs to complete, at which time the ratio of two isomers (8a:8b) was 6:1. This mixture was treated with HCl to afford the ketone 9. When the Heck reaction time was increased to 48 hrs, equilibrium was reached to give the ratio of two isomers (8a:8b) at 1.7:1. After the hydrolysis with HCl and the preparative HPLC purification, the ketone 9b was obtained.

1.2 Double Bond Migration Observed

The triflate 7 was converted to a mixture of two isomeric enol vinyl ethers 8a and 8b via a Heck coupling reaction. A partial double bond shift observed during the Heck reaction (Scheme 3)

Scheme 3

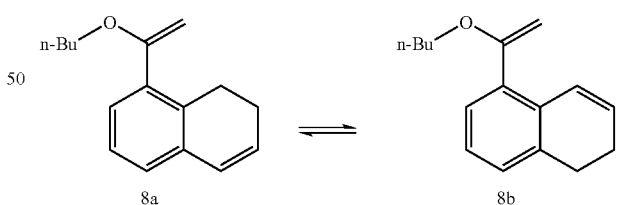

Table 1 shows the isomerization ratio of 8a and 8b versus Heck reaction time. "Isomer A"=Compound 8a. "Isomer B"=Compound 8b.

TABLE 1

| Time | 16 h | 23 h | 39 h | 47 h | 62 h |
|---|---|---|---|---|---|
| Isomer A | 85.7% | 80.0% | 72.2% | 63.0% | 63.0% |
| Isomer B | 14.3% | 20.0% | 27.8% | 37.0% | 37.0% |

Subsequent hydrolysis of 8a and 8b with HCl produced ketones 9a and 9b, respectively. Preparative HPLC purification of ketones 9a and 9b resulted in clean preparations of 9a and 9b (See Scheme 2.)

1.3 Synthesis of Phenylpropan-1-Amine 3-(3-Trifluoromethyl-phenyl)-propylamine (13) is not commercially available and was prepared as follows (Scheme 5). Commercially available trans-3-(trifluoromethyl)-cinnaomyl chloride (10) was treated with NH$_4$OH to give the desired amide 11. The double bond was reduced by hydrogenation LAH reduced the amide 12 to afford the amine 13

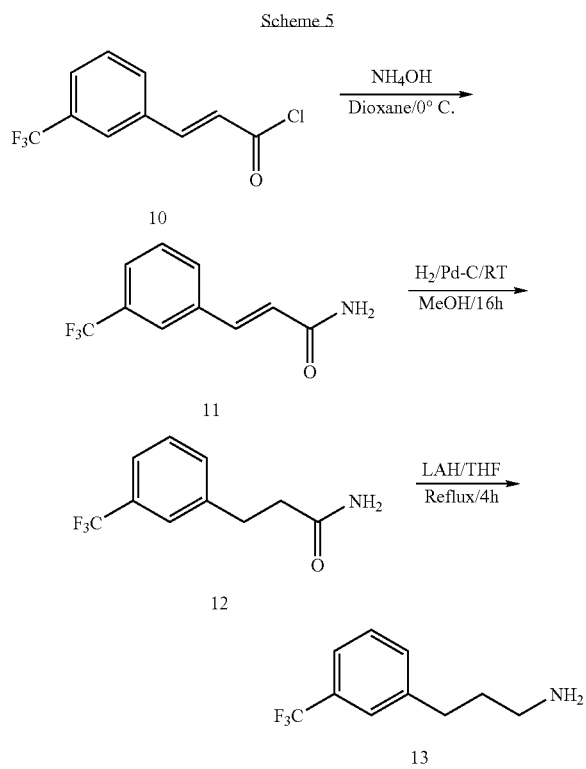

1.4 Reductive Amination

To complete the syntheses, reductive amination was performed (Scheme 6) to form compound 1 from 9a+13, and compound 2 from 9b+13.

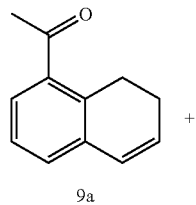

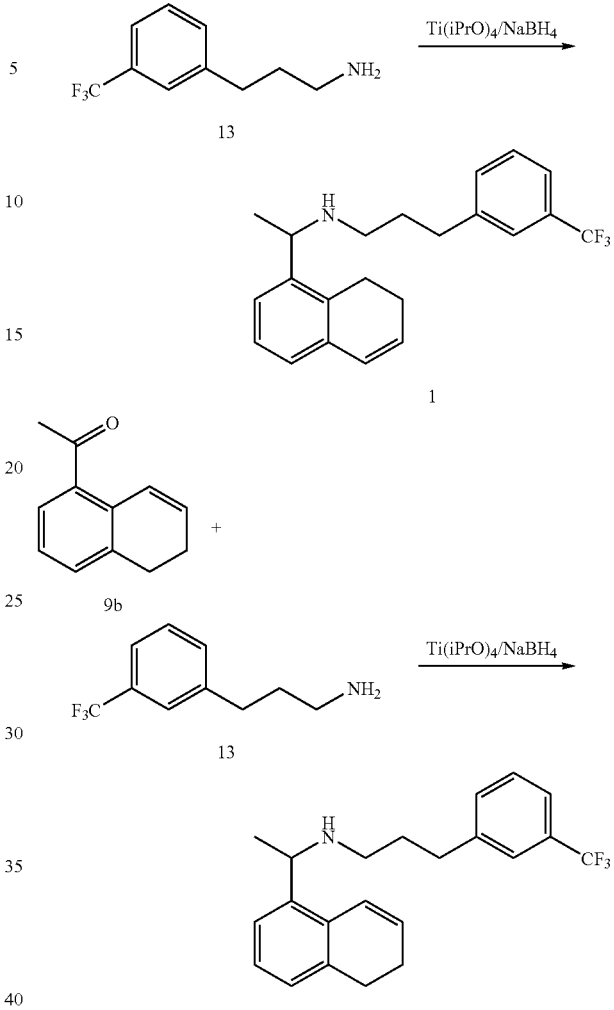

Stepwise reductive amination was employed. The amine 13 and the ketone 9 was mixed in neat (Ti(OiPr)$_4$) overnight and the resulting imine was reduced by NaBH$_4$ in MeOH to give the desired compound 1 and 2 from 9a and 9b respectively.

1.5 Chiral Separation

Preparative chiral HPLC purification of compounds 1 and 2 produced the desired enantiomerically pure isomers. Their spectroscopic data matched with those of the isolated compounds in every aspect.

Compounds 1 and 2 were separated from a single composition using a 150×4.6 mm Chirobiotic V HPLC column. The mobile phase was MeOH/HOAc/TEA 1000/0.2/0.2 (v:v:v) and a flow rate of 1 ml/min at ambient temperature with a detection wavelength of 260 nm. FIG. 1 shows an exemplary HPLC graph of the separation of compounds 1 and 2 using the above chiral HPLC. Collection of individual peaks and spectroscopic analysis confirmed the indicated peaks matched those of the isolated compounds in every respect. Other chiral separation methods known to those skilled in the art may also be used to chirally separate compound 1 and 2.

2. Synthetic Method II: Asymmetric Synthesis

2.1 Asymmetric Reduction

The inventors identified synthetic methods for achieving asymmetric reduction and chiral transformation of compounds 9a and 9b. (Scheme 7).

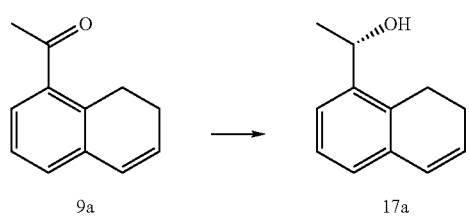

Scheme 7

Various synthetic schemes were screened to achieve asymmetric reduction of Scheme 7. Methyl oxazaborolidine catalyzed borane reduction (Me—CBS/BH$_3$ or Me—CBS/catecholborane) was effective for the chiral transformation. For example, with [(R)-Me—CBS (1 eq), BH$_3$—THF (1 eq), toluene], the alcohol 17a was obtained (Scheme 8).

Scheme 8

2.2 Alternative Symmetric Synthesis of Compound 9a

Compound 9a was also synthesized using Scheme 2 resulting in a mixture comprising both compounds 9a and 9b. Chiral separation methods may then be used to isolate and purify compound 9a from the mixture.

Another method for symmetric synthesis of compound 9a avoids the need for the chiral separation methods of Scheme 2 and resulted in a high yield of purified compound 9a. The triflate 4 was subjected to the Heck coupling condition of Example 1.1 to afford 15. HCl hydrolysis of the vinyl ether and the reduction of the ketone followed by elimination produced the ketone 9a (Scheme 9). Compound 9a can then undergo chiral transformation to compound 17a as described in Scheme 8.

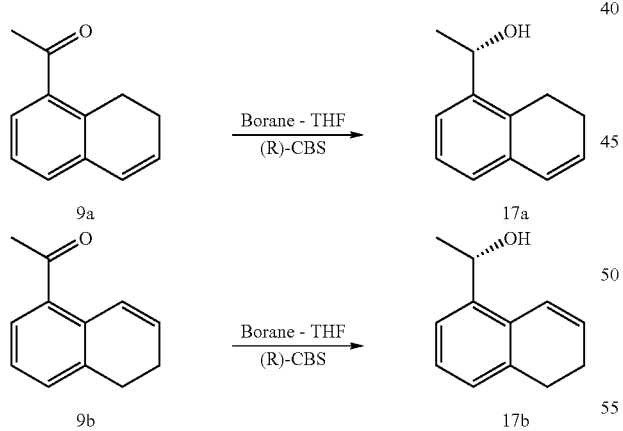

Scheme 9

2.3 Synthesis of Aldehyde

Synthesis of aldehyde required for synthesis of compounds 1 and 2 in examples 2.4 and 2.5 is described in Scheme 10.

Scheme 10

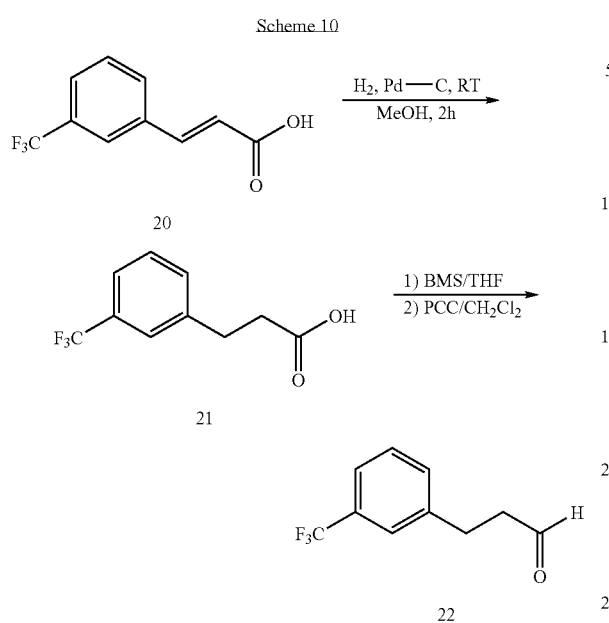

2.4 Asymmetric Synthesis of Compound 1

Synthesis of compound 1 from compound 9a is described in Scheme 11. The alcohol 17a was converted to the azide 18a using (PhO)$_2$PON$_3$, which was then reduced to 19a using the conventional Ph$_3$P condition. Reductive amination with the aldehyde 22 afforded 1.

Scheme 11

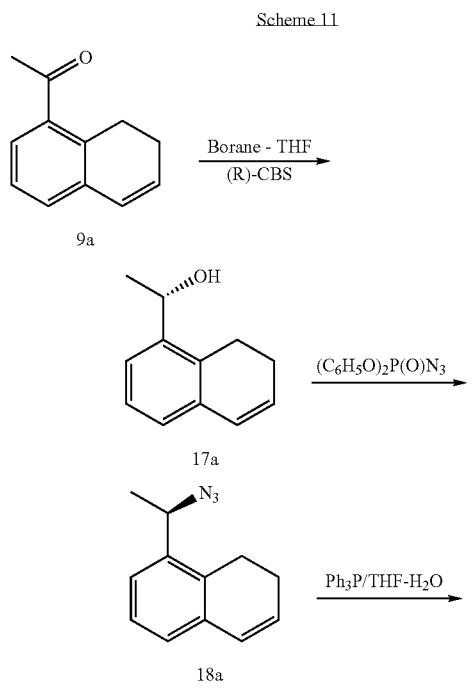

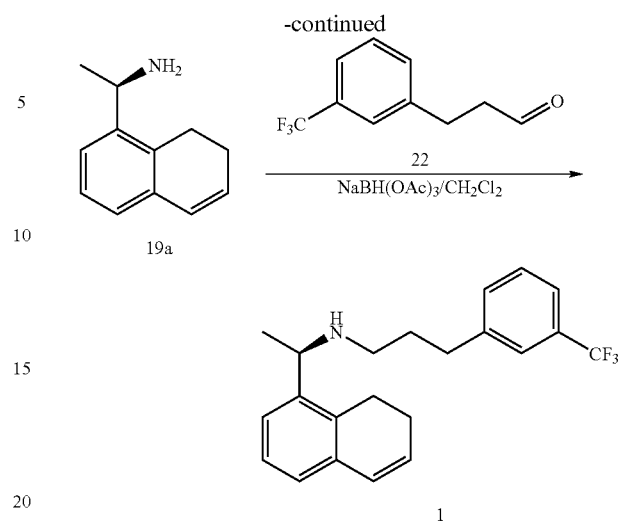

2.5 Asymmetric Synthesis of Compound 2

Synthesis of compound 2 from compound 9b is described in Scheme 12. The alcohol 17b was converted to the azide 18b using (PhO)$_2$PON$_3$, which was then reduced to 19b using the conventional Ph$_3$P condition. Reductive animation with the aldehyde 22 afforded 2.

Scheme 12

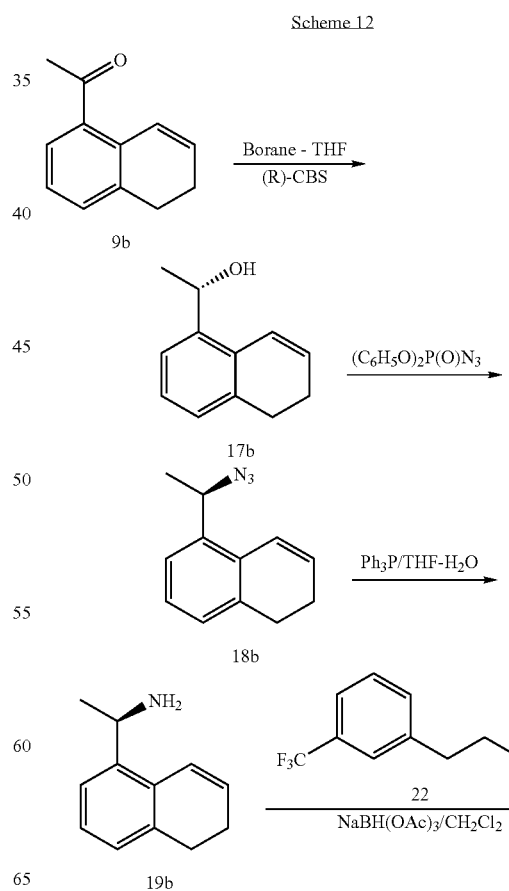

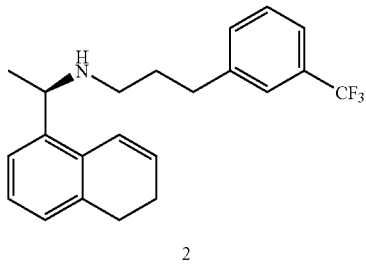

2

3. Synthetic Examples of Compounds in Schemes

Compound (6): 1,2,3,4-Tetrahydro-naphthalene-1,5-diol

To a solution of 5-hydroxyl-tetralone (5.0 g, 30.8 mmol) in methanol (50 mL) at 0° C. was added sodium borohydride (2.1 g, 55.5 mmol). The reaction was stirred at 0° C. for 30 min, then warmed up to room temperature. Stirring was continued for 1 hour. The reaction mixture was evaporated to dryness. Ethyl acetate was added and the mixture was washed with saturated $NaHCO_3$ and dried over $MgSO_4$. Evaporation gave compound 6 as an off-white solid. (4.7 g, 93%). $^1HNMR$(300 $MH_2$, $CDCl_3$); 1.51 (2 H, m) 1.72 (2 H, m), 2.39 (2 H, m), 4.32 (1 H, m), 4.80 (1 H, d), 6.50 (1 H, d), 6.72 (1 H, d), 6.81 (1 H, t), 8.98 (1 H, s). M/S: 164.

Compound (7): Trifluoro-methanesulfonic acid 7,8-dihydro-naphthalen-1-yl ester To a suspension of 1,2,3,4-Tetrahydro-naphthalene-1,5-diol (6) (3.5 g, 21.3 mmol), triethylamine (6.2 mL, 44.8 mmol) in dichloromethane (100 mL) at −2° C. was added dropwise a solution of traflate anhydride (7.5 mL, 44.8 mmol) in dichloromethane (7.5 mL). During addition, the reaction was kept below 0° C. and a light yellow solution was formed. After addition, the reaction turned light brown. The reaction was stirred at 0° C. for 1 hour, then quenched by saturated sodium bicarbonate solution (100 mL) at 0° C. Dichloromethane (200 mL) was added and the organic layer was separated. After washing by brine, and drying over $MgSO_4$, the organic layer was evaporated to dryness to give a brownish oil. Purification was performed by flash chromatography on silica gel, loaded and eluted with 5% dichloromethane in hexane. Pure fractions were combined and evaporated to give compound 7 as a colorless oil. (3.5 g, 46%). 1 HNMR (300 MHz, CDCl3); 2.35 (2 H, m), 2.89 (2 H, t), 6.11 (1 H, dt), 6.61 (1 H, d), 7.01 (1 H, d), 7.08 (1 H, m). 7.15 (1 H, m), 13CNMR(75 MH2, CHCl3): 21.3, 22.5, 112.7, 116.9, 120.1, 121.2, 125.4, 126.1, 127.2, 127.9,128.3, 130.7, 137.3, 147.5.

Compounds (9a, 9b): 1-(7,8-Dihydro-naphthalen-1-yl)-ethanone and 1-(5,6-Dihydro-naphthalen-1-y])-ethanone To a solution of trifluoro-methanesulfonic acid 7,8-dihydro-naphthalen-1-yl ester (7) (2.2 g, 7.92 mmol) in DMF was added triethylamine (2.2 mL, 15.8 mmol) and n-butylvinylether (4.1 mL, 31.7 mmol) at room temperature. The reaction was bubbled with nitrogen for 10 min, followed by palladium acetate (107 mg, 0.48 mmol) and 1,3-dppp (200 mg, 0.48 mmol). The reaction was heated to 60° C. and the stirring was continued for 6 hour. The reaction was cooled to room temperature. Ethyl ether (100 mL) was added and the solution was washed with saturated sodium bicarbonate solution, brine and dried over MgSO4. Evaporation gave a brown oil. The crude oil was loaded a silica gel pat and eluted with 10% dichloromethane in hexane. The filtrate was evaporated to give a colorless oil (1.22 g, 67%). NMR showed there were two isomers in the product.

The oil was dissolved in acetone (10 mL). 3NHCl solution (10 mL) was added at room temperature. The reaction was stirred at room temperature for 1 hour. Dichloromethane (100 mL) was added, followed by saturated sodium bicarbonate solution. The organic layer was separated and washed by brine and dried over MgSO4. Evaporation gave a colorless oil. Purification was performed by chromatography on silica gel, loaded and eluted with 50% dichloromethane in hexane. Pure fractions were combined and evaporated to give a colorless oil. (920 mg, 100%). HPLC showed two isomers (9a:9b=5:1).

The two isomers were separated by chromatography. Compound 9a: 1HNMR (300 MHz, CDCl3): 2.25 (2 H, dt), 2.57 (3 H, s), 3.01 (2 H, t), 6.05 (1 H, dt), 6.45 (1 H, d), 7.12 (1 H, d), 7.19 (1 H, dd), 7.45 (1 H, d). 13CNMR (75 MHz, CDCl3): 23.2, 24.6, 30.4, 125.6, 127.1, 127.3, 127.9, 129.5, 135.3, 135.7, 138.2, 202.8. Compound 9b: 1HNMR(300 MHz, CLCl3): 2.21 (2 H, m), 2.59 (3 H, s), 2.79(1 H, t), 6.15 (1 H, dt), 7.02 (1 H, d), 7.12 (1 H, d), 7.19 (1 H, dd), 7.45 (1 H, d). 13CNMR (75 MHz, CDCl3): 22.3 28.1, 29.9, 125.6, 127.1, 127.3, 127.9, 129.5, 135.3, 135.7, 138.2, 202.1

Compound (4): Trifluoro-methanesulfonic acid 5-oxo-5,6,7,8-tetrahydro-naphthalen-1-yl ester To a suspension of 5-hydroxy-l-tetralone (10.0 g, 61.7 mmol) and pyridine (5.5 mL, 67.9 mmol) in dichloromethane (200 mL) at −2° C. was added dropwise a solution of traflate anhydride (11.4 mL, 67.9 mmol) in dichloromethane (11.4 mL). During addition, the reaction was kept below 0° C. After addition, the reaction turned light brown. The reaction was stirred at 0° C. for 1 hour, then evaporated to dryness to give a brown oil. Purification was performed by flash chromatography on silica gel, loaded and eluted with 10% dichloromethane in hexane. Pure fractions were combined and evaporated to give compound 4 as a colorless oil. (16.2 g, 94%).

Compound (14): 5-(1-Butoxy-vinyl)-3,4-dihydro-2H-naphthalen-1-one

To a solution of trifluoro-methanesulfonic acid 5-oxo-5,6,7,8-tetrahydro-naphthalen-1-yl ester (4)(15.0, 53.9 mmol) in DMF was added triethylamine (15.0 mL, 107.8 mmol) and butylvinylether (27.9 mL, 215.8 mmol) at room temperature. The reaction was bubbled with nitrogen for 10 minutes, followed by palladium acetate (726 mg, 3.2 mmol) and 1,3-bis(diphenylphosphine)propane or 1,3-dppp (1.3 g, 3.2 mmol). The reaction was heated to 60° C. and the stirring was continued for 24 hour. The reaction was cooled to room temperature. Ethyl ether (500 mL) was added and the solution was washed with saturated sodium bicarbonate solution, brine and dried over MgSO4. Evaporation gave a brownish oil. The crude oil was loaded a silica gel and eluted with 10% ethyl acetate in hexane. The filtrate was evaporated to give compound 14 as a colorless oil (10.4 g, 79%). Compound 14: $^1HNMR$(300 MHz, $CDCl_3$): 0.95 (2 H, t), 1.05 (3 H, t), 1.58 (2 H, m), 1.85 (2 H, m), 2.10 (2 H, m), 2.65 (2 H, t), 3.01 (2 H, t), 4.30 (2 H, d), 7.25 (1 H, dd), 7.50 (1 H, d), 7.19 (1 H, dd), 7.45 (1 H, d). 8.10 (1 H, d).

Compound (15): 1-(5-Hydroxy-5,6,7,8-tetrahydro-naphthalen-1-yl)-ethanone

To a solution of 5-(1-butoxy-vinyl)-3,4-dihydro-2H-naphthalen-1-one (14)(10.0 g, 41.0 mmol) in methanol (200 mL) at 0° C. was added sodium borohydride (1.5 g, 41.0 mmol) in portion. The reaction was stirred at 0° C. for 10 min, then warmed to room temperature. Stirring was continued for 1 hour. Saturated sodium bicarbonate solution was added to quench the reaction and followed by the addition of ethyl acetate (500 mL). The organic layer was washed by brine and dried over MgSO4. Evaporation gave a crude oil. The product was dissolved in acetone (100 mL) and 3 N HCl (100 mL) was added. The reaction mixture was stirred at room temperature for 1 hour and evaporated to dryness. Purification was performed by chromatography on silica gel, eluted with ethyl acetate in hexane (30% to 50% gradient). Pure fractions were combined and evaporated to give compound 15 as a pale yellow oil(7.2 g, 92%). $^1$HNMR(300 MHz, CDCl$_3$): 1.62-2.05 (4 H, m), 2.55 (3 H, s), 2.81-3.15 (2 H, m), 4.75 (1 H, dt), 7.22 (1 H, t), 7.55 (1 H, d), 7.57 (1 H, d).

Compound (9a): 1-(7,8-Dihydro-naphthalen-1-yl)-ethanone

To a suspension of 1-(5-hydroxy-5,6,7,8-tetrahydro-naphthalen-1-yl)-ethanone (15) (7.2 g, 37.9 mmol) and triethylamine (5.3 mL, 37.9 mmol) in dichloromethane (100 mL) at 0° C. was added dropwise a solution of triflic anhydride (6.4 mL, 37.9 mmol) in dichloromethane (7.5 mL). During addition, the reaction was kept below 0° C. and a brownish solution was formed. The reaction was stirred at 0° C. for 1 hour, then quenched by saturated sodium bicarbonate solution (100 mL) at 0° C. Dichloromethane (200 mL) was added and the organic layer was separated. After washing with brine and drying over MgSO$_4$, the organic layer was evaporated to dryness to give a brownish oil. Purification was performed by flash chromatography on silica gel, eluting with 10% dichloromethane in hexane. Pure fractions were combined and evaporated to give compound 9a as a colorless oil. (2.6 g, 40%), Compound 9a: $^1$HNMR(300 MHz, CDCl$_3$): 2.25 (2 H, dt), 2.57 (3 H, s), 3.01 (2 H, t), 6.05 (1 H, dt), 6.45 (1 H, d), 7.12 (1 H, d), 7.19 (1 H, dd), 7.45 (1 H, d). $^{13}$CNMR (75 MHz, CDCl$_3$): 23.2, 24.6, 30.4, 126.2, 127.4, 127.9, 129.5, 130.2, 135.3, 135.7, 138.2, 203.4

Compound (11): 3-Trifluoromethyl-cinnamamide

Trans-3-(trifluoromethyl)-cinamoyl chloride (5.0 g, 21.3 mmol) was dissolved in dioxane (18 mL) and the resulting solution was added dropwise to a solution of ammonium hydroxide in water (28%-30%, 25.7 mL, 213 mmol) at 0° C. After the addition was completed, the mixture was allowed warm to room temperature. Water (50 mL) was added and the resulting white solid was obtained after filtration. The wet solid was dried under vacuum to give compound 11 as a white solid (4.2 g, 92.6%).

Compound (12): 3-(3-Trifluoromethyl-phenyl)-propionamide

To a solution of 3-trifluoromethyl-cinnamamide (11) (4.2 g, 19.5 mmol) in methanol (50 mL) at room temperature under nitrogen was added 10% palladium on carbon (420 mg). The reaction mixture was purged to hydrogen three times. A hydrogen balloon was connected to the reaction. Hydrogenation was maintained overnight. The reaction was purged by nitrogen, then filtered through Celite. The filtrate was evaporated to give compound 12 as a white solid (3.75 g, 88.6%).

Compound (13): 3-(3-Trifluoromethyl-phenyl-propylamine

To a solution of 3-(3-trifluoromethyl-phenyl)-propionamide (12) (3.4 g, 15.7 mmol) in THF (70 mL) was added dropwise a solution of lithium aluminum hydride in THF (1.0 M, 15.7 mL, 15.7 mmol) at room temperature. The reaction mixture was heated to reflux for 4 hours, then cooled to 0° C. Ethyl acetate was added to quench the reaction. Sodium hydroxide (5 N) was added and the mixture was refluxed for 30 min. The reaction was cooled to room temperature. Ethyl acetate was added to extract the product. The organic layer was separated and washed by saturated sodium bicarbonate and brine, then dried over MgSO$_4$. Evaporation gave a crude oil, which purified by chromatography to give compound 13 as a colorless oil (1.6 g, 50.2%).

Compound (1): [1-(7,8-Dihydro-naphthalen-1-yl)-ethyl]-[3-(3-trifluoromethyl-phenyl)-propyl]-amine hydrochloride The mixture of 1-(7,8-dihydro-naphthalen-1-yl)-ethanone (10) (172 mg, 1.0 mmol) and 3-(3-trifluoromethyl-phenyl)-propylamine (13) (204 mg, 1.0 mmol) in titanium (IV) isopropoxide (1 mL) was stirred at room temperature overnight. Methanol(5 mL) was added followed by addition of sodium borohydride (55 mg, 2.0 mmol). The reaction mixture was stirred at room temperature for 1 hour and evaporated to dryness. The crude product was purified by chromatography on silica gel, loaded with dichloromethane and eluted with 2% methanol in dichloromethane containing 0.5% ammonium hydroxide. The pure fractions were combined and evaporated to give a colorless oil. The product was converted to a hydrochloride salt by addition of 1 N HCl in ethyl ether. Evaporation gave compound (1) as an off-white solid (325 mg, 82.2%).

Compound (2): [1-(5,6-Dihydro-naphthalen-1-yl)-ethyl])-[3-(3-trifluoromethyl-phenyl)-propyl]-amine The mixture of 1-(5,6-dihydro-naphthalen-1-yl)-ethanone (9b) (172 mg, 1.0 mmol) and 3-(3-trifluoromethyl-pheny)-propylamine (13) (204 mg, 1.0 mmol) in titanium(IV) isopropoxide (1 mL) was stirred at room temperature overnight. Methanol (5 mL) was added followed by careful addition of sodium borohydride (55 mg, 2.0 mmol). The reaction mixture was stirred at room temperature for 1 hour, then evaporated to dryness. The crude product was purified by chromatography on silica gel, loaded with dichloromethane and 30% ethyl acetate in hexane. The pure fractions were combined and evaporated to give compound (2) as a colorless oil (279 mg, 78%).

4. Separation of Isomers 1 and 2

Separation Results

Separation of the two position isomers (1 and 2) was accomplished using preparative chromatography. Various chromatographic medias such as normal phase silica gel, silver nitrated impregnated silica gel, reverse phase C-18 and chiral phases were tried in order to develop a method to separate these two isomers. Only a slight separation with a resolution (Rs) <1.1 was evident on the several reverse phase C-18 columns. Therefore, a recycling technique was used in preparative chromatography to enhance the separation efficiency. The Waters, X-terra C-18 with imbedded polar group was used as the preparative column. 8 g of total product was made and 1.5 g of compound 2 and 4.5 g of compound 1 were generated after the purification.

The chromatographic separation was achieved on the Waters, X-terra C-18 RP, 5 cm (i.d.)×30 cm (length), column by using the Varian Pro-star preparative system consisting of two high pressure pumps with an automated recycling future. 8 g of total product was received and the total product was contained the two desired isomers at a ratio of 1 (compound 2) to 2.5 (compound 1) and some minor impurities. A total of fifteen injections were made on the preparative column at 0.35 g per injection. The total product was dissolved in Acetonitrile/Water (70/30) at the concentration of 22 mg/ml. Sample was injected through a sample pump at the injection flow rate of 35 ml/min. The separation was carried out at isocratic condition with a mobile phase of Acetonitrile/Water (45/55). The eluant was recycled into the same column until the two peaks were clearly separated. Three recycling cycles were required to separate these two isomers. The undesired impurities were shaved off during the recycling cycles. The eluant was then collected using an automatic fraction collector and the fraction containing the desired products was analyzed with an analytical HPLC system. The wet fractions were blown with N2 to remove the acetonitrile and then extracted with CH2CL2 and blow with N2 to dryness. N2 was used since the sample was not stable under oxygen.

Separation conditions were as follows:

| Column | X-terra C-18 RP, 10 u |
|---|---|
| Column size | 5 cm × 30 cm |
| Particle size | 10 u |
| Wavelength | 220 nm |
| Cycle time/per cycle | 20 min |
| Total separation time for each injection | 80 min |
| Sample loading/per injection | 0.55 g |
| Mobile phase | 45/55/Acetonitrile/Water |
| Temperature | 25 C. |
| Sample concentration | 22 mg/ml |
| Injection volume | 25 ml |
| Flow rate | 120 ml/min |

Results for 3 samples:

| Sample # | Purified Material weight | Purity by Area % |
|---|---|---|
| 1 | Compound 2, 1.5 g | about 96% |
| 2 | Compound 1, 4.5 g | about 98% |
| 3 | Overlap, 1.2 g | enriched with peak-1 |

5. NMR Data

NMR Summary $^1$H and $^{13}$C NMR assignment were obtained on a sample of the structure below.

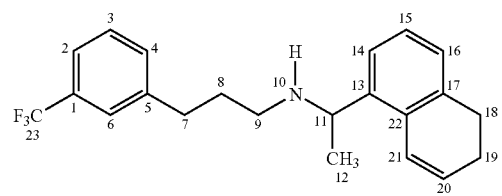

Full assignment of the $^1$H spectrum was achieved. All carbons in the molecules were also assigned chemicals shift values except for those in the 23 and 1 positions. Those carbons were not detected because of the combination of relatively low sample concentration and the fact that they would form a well-resolved quartet distributing the carbon signal intensity among four peaks. Exact mass measurement confirmed the molecular formula as $C_{22}H_{24}NF_3$. The NMR data together with the molecular formula information provides definitive evidence to support the above structure.

NMR Materials and Methods

The sample was dissolved in $CDCl_3$, and spectra obtained at 30° C. on a Bruker DPX400 NMR spectrometer 1D proton and carbon-13 spectra and, 2D, COSY, NOESY, $^1H/^{13}C$ HMQC and $^1H/^{13}C$ HMBC datasets were obtained.

NMR Results and Discussions

The proton NMR spectrum is consistent with the structure assigned by obtaining 1H-1H connectivities from the COSY and NOESY spectra. Full assignment of the protons on the 1,3 di-substituted benzene moiety of the molecule was achieved via multiple bond 1H-13C correlations from the HMBC experiment. The non-quaternary carbons were assigned using the HMQC experiment. The HMBC experiment was used to assign the quaternary carbons. The assignments are summarized in the table below.

TABLE 3

Proton and Carbon-13 NMR chemical shifts of Compound 1 in $CDCl_3$ at 30° C..

| Positional number | Proton chemical shift (ppm) | Carbon-13 chemical shift (ppm) |
|---|---|---|
| 1 | — | — |
| 2 | 7.34 (1H, d) | 123.0 |
| 3 | 7.38 (1H, t) | 129.0 |
| 4 | 7.44 (1H, d) | 132.2 |
| 5 | — | 143.5 |
| 6 | 7.43 (1H, s) | 125.5 |
| 7 | 2.55 (2H, m) | 33.8 |
| 8 | 1.83 (2H, m) | 32.2 |
| 9 | 2.71 (2H, m) | 47.5 |
| 10 | — | — |
| 11 | 4.16 (1H, q) | 53.6 |
| 12 | 1.35 (3H, d) | 23.8 |
| 13 | — | 140.6 |
| 14 | 7.32 (1H, d) | 124.0 |
| 15 | 7.15 (1H, t) | 127.3 |
| 16 | 7.02 (1H, d) | 126.5 |
| 17 | — | 136.5 |
| 18 | 2.81 (2H, t) | 28.9 |
| 19 | 2.29 (2H, m) | 23.0 |
| 20 | 6.14 (2H, m) | 129.7 |
| 21 | 6.84 (2H, d) | 123.9 |
| 22 | — | 131.7 |
| 23 | — | — |

Proton numbers, multiplicity (s = singlet, d = doublet, t = triplet, q = quartet, m = complex multiplicity) are shown in parentheses.

What is claimed is:

1. A compound chosen from

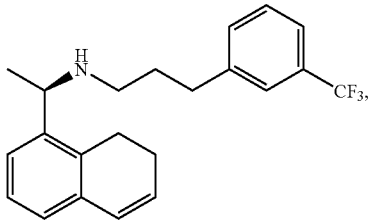 (1)

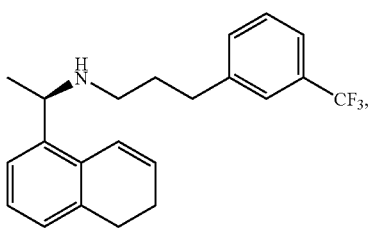 (2)

optionally substituted derivatives thereof, isomers thereof, solvates thereof, or salts thereof.

2. A composition comprising at least one compound chosen from

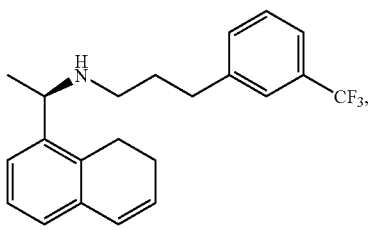 (1)

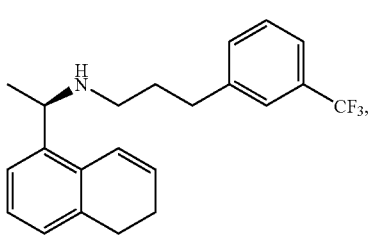 (2)

optionally substituted derivatives thereof, isomers thereof, solvates thereof, or salts thereof;
and at least one acceptable carrier 3. A process for the preparation of at least one dihydronaphthalene compound wherein the process comprises reacting at least one compound A with at least one compound B, wherein
compound A is chosen from

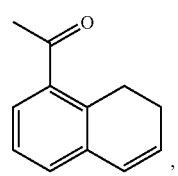 (9a)

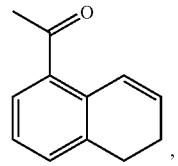 (9b)

optionally substituted derivatives thereof, isomers thereof, solvates thereof, salts thereof, and mixtures thereof; and
compound B is chosen from

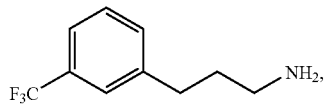 (13)

optionally substituted derivatives thereof, isomers thereof, solvates thereof, salts thereof, and mixtures thereof,
wherein compounds A and B react to form a dihydronaphthalene compound.

4. The process according to claim 3, wherein the at least one dihydronaphthalene compound formed is

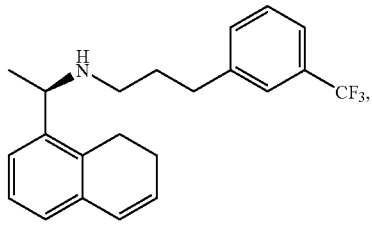 (1)

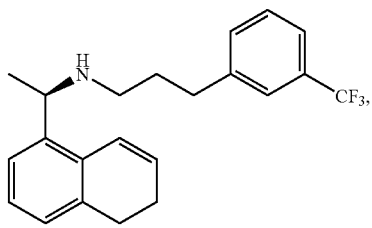 (2)

or mixtures thereof.

5. The process according to claim 3, wherein compound A is formed by reacting

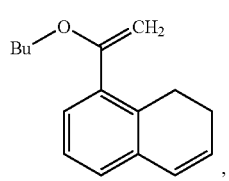 8a

-continued

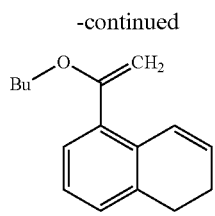

isomers thereof, optionally substituted derivatives thereof, or mixtures thereof with an acid.

6. The process according to claim 5, wherein the acid is HCl.

7. The process according to claim 5, wherein

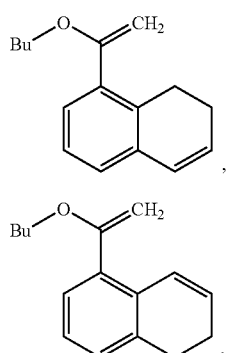

isomers thereof, optionally substituted derivatives thereof, or mixtures thereof are formed by reacting at least one compound C with at least one compound D, wherein
C is chosen from

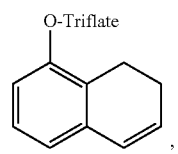

isomers thereof, and optionally substituted derivatives thereof; and
compound D is chosen from

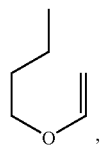

isomers thereof, and optionally substituted derivatives thereof.

8. The process according to claim 7, wherein at least one compound C is reacted with at least one compound D in the presence of a catalyst.

9. The process according to claim 8, wherein at least one compound C is reacted with at least one compound D in the presence of a catalyst comprising palladium.

10. The process according to claim 7, wherein

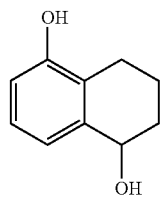

is reacted with triflate anhydride and tetraethylamine in dichloromethane to form

11. The process according to claim 10 wherein

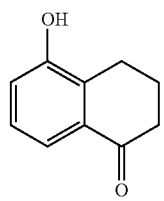

is reacted with NaBH₄ and MeOH to form

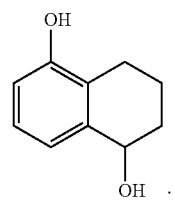

12. The process according to claim 7, wherein

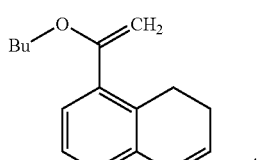

and

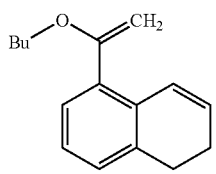

are formed at an 8a:8b weight ratio ranging from 10:1 to 1:2.

13. The process according to claim 12, wherein compounds 8a and 8b are formed at a 8a:8b weight ratio ranging from 9:1 to 1:1.

14. The process according to claim 13, wherein compounds 8a and 8b are formed at a 8a:8b weight ratio ranging from 3:1 to 1.5:1.

15. The process according to claim 9, wherein compounds 9a and 9b are separated and purified using chromatography.

16. The process according to claim 11, wherein compound 9a and 9b are separated and purified using chiral HPLC.

17. The process according to claim 4, wherein compound 1, compound 2, or mixtures thereof are separated and purified using chromatography.

18. The process according to claim 17, wherein compound 1 and compound 2 are separated and purified using chiral HPLC.

19. The process according to claim 3, wherein

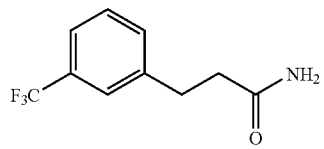

is reduced with lithium aluminum hydride to form

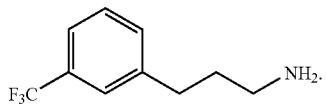

20. The process according to claim 19, wherein

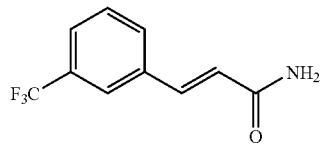

is reduced by hydrogenation to form

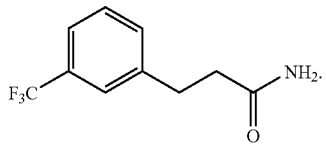

21. The process according to claim 20, wherein

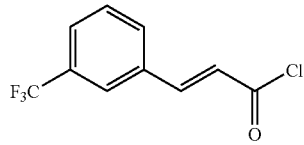

is reacted with NH₄OH to form

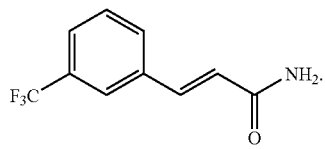

22. A process for the preparation of at least one dihydronaphthalene compound wherein the process comprises reacting at least one compound E with at least one compound G, wherein compound E is chosen from

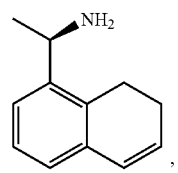

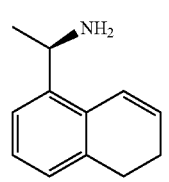

isomers thereof, and optionally substituted derivatives thereof; and compound G is chosen from

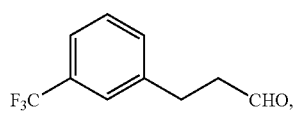

isomers thereof, and optionally substituted derivatives thereof, wherein compounds E and G react to form a dihydronaphthalene compound.

23. The process according to claim 22, wherein the at least one dihydronaphthalene compound formed is

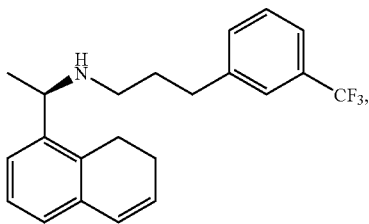
(1)

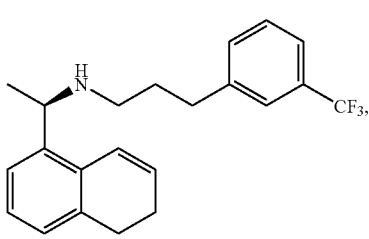
(2)

or mixtures thereof.

24. The process according to claim 22, wherein the process comprises forming compound E from

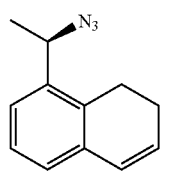
18a

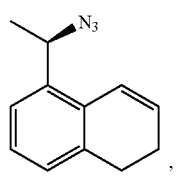
18b isomers thereof, optionally substituted derivatives thereof, or mixtures thereof reduction.

25. The process according to claim 24, wherein compound E is formed by reducing

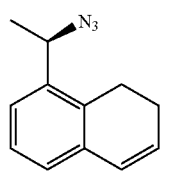
18a

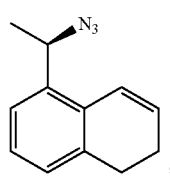
18b isomers thereof, optionally substituted derivatives thereof, or mixtures thereof in the presence of Ph$_3$P.

26. The process according to claim 25, wherein

18a

18b isomers thereof, optionally substituted derivatives thereof, or mixture thereof are formed by converting

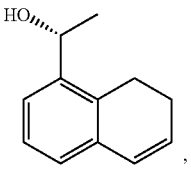
17a

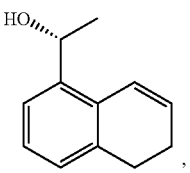
17b isomers thereof, optionally substituted derivatives thereof, or mixtures thereof to an azide using (PhO)$_2$PON$_3$.

27. The process according to claim 26, wherein

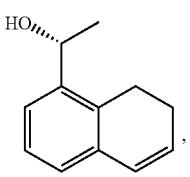
17a

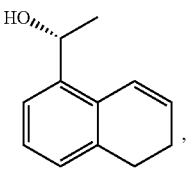
17b isomers thereof, optionally substituted derivatives thereof, or mixtures thereof are formed by reducing

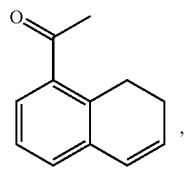, 9a

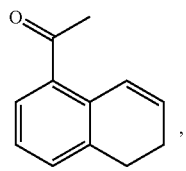, 9b isomers thereof, optionally substituted derivatives thereof, or mixtures thereof to an alcohol using a borane reduction.

28. The process according to claim 27, wherein the borane reduction is catalyzed by methyl oxazaborolidine.

29. The process according to claim 27, wherein

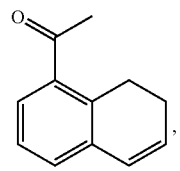 9a isomers thereof, or optionally substituted derivatives thereof, or mixtures thereof are formed by reacting

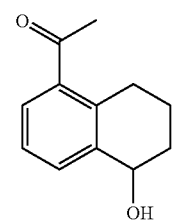 16 with triflate anhydride and tetraethylamine in dichloromethane followed by elimination of the hydroxyl group.

30. The process according to claim 29, wherein

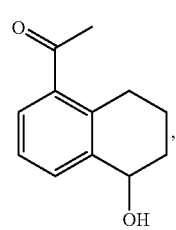 16 isomers thereof, or optionally substituted derivatives thereof, or mixtures thereof are formed by reacting

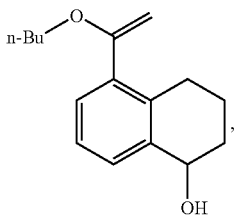 15 isomers thereof, optionally substituted derivatives thereof, or mixtures thereof with an acid.

31. The process according to claim 30, wherein the acid is HCl.

32. The process according to claim 30, wherein

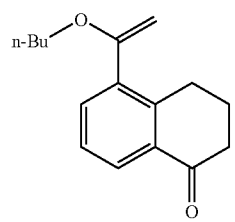 14 is reacted with NaBH₄ and MeOH to form

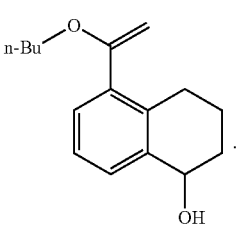 15

33. The process according to claim 32, wherein

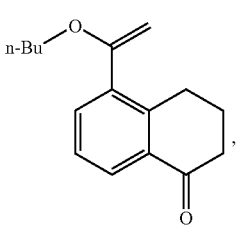 14 isomers thereof, optionally substituted derivatives thereof, or mixtures thereof are formed by reacting

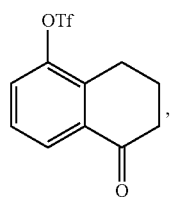

isomers thereof, and optionally substituted derivatives thereof, with

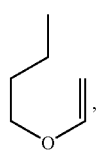

isomers thereof, and optionally substituted derivatives thereof.

34. The process according to claim 33, wherein reacting

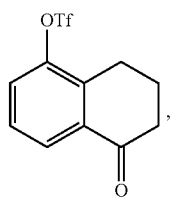

isomers thereof, and optionally substituted derivatives thereof, is in the presence of a catalyst.

35. The process according to claim 34, wherein the catalyst comprises palladium.

36. The process according to claim 33, wherein

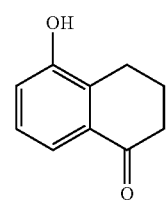

is reacted with triflate anhydride and tetraethylamine in dichloromethane to form

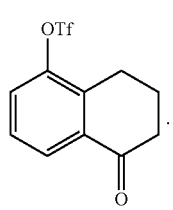

37. The process according to claim 27, wherein

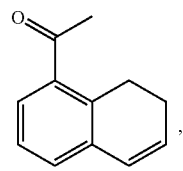

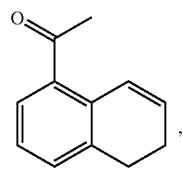

isomers thereof, optionally substituted derivatives thereof, or mixtures thereof are formed by reacting

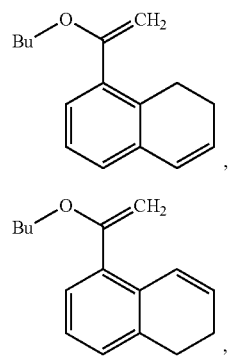

isomers thereof, optionally substituted derivatives thereof, or mixtures thereof with an acid.

38. The process according to claim 37, wherein the acid is HCl.

39. The process according to claim 37, wherein

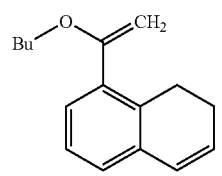

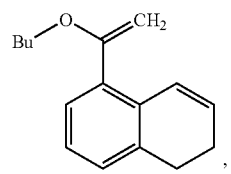

isomers thereof, optionally substituted derivatives thereof, or mixtures thereof are formed by reacting at least one compound C with at least one compound D, wherein
compound C is chosen from

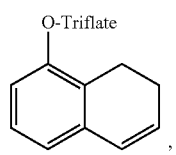

isomers thereof, and optionally substituted derivatives thereof; and
compound D is chosen from

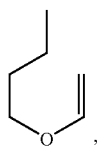

isomers thereof, and optionally substituted derivatives thereof.

40. The process according to claim 39, wherein the at least one compound C reacts with at least one compound D in the presence of a catalyst.

41. The process according to claim 40, wherein at least one compound C reacts with at least one compound D in the presence of a catalyst comprising palladium.

42. The process according to claim 39, wherein

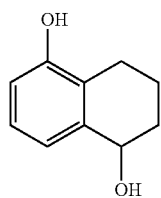

is reacted with triflate anhydride and tetraethylamine in dichloromethane to form

43. The process according to claim 42, wherein

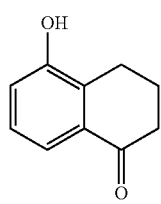

is reacted with NaBH₄ and MeOH to form

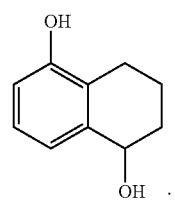

44. The process according to claim 22, wherein

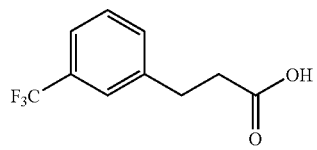

is reduced to form

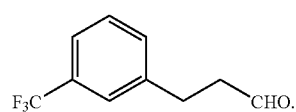

45. The process according to claim 44, wherein

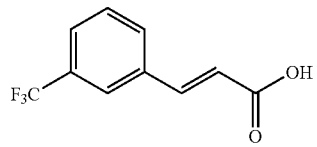

is reduced by hydrogenation to form

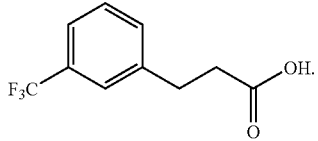

46. The process according to claim 23, wherein only one of compound 1 or compound 2 is formed.

47. The process according to claim 45, wherein compound 1, compound 2, or mixtures thereof are purified without the use of chiral HPLC.

48. A process for the preparation of a dihydronaphthalene compound wherein the process comprises reacting at least one compound E with at least one compound G, wherein compound E is chosen from

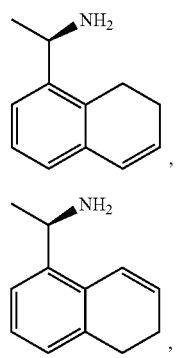

optionally substituted derivatives thereof, isomers thereof, solvates thereof, and salts thereof; and
compound G is chosen from

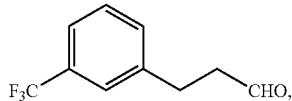

optionally substituted derivatives thereof, isomers thereof, solvates thereof, and salts thereof, wherein compounds E and G react to form a dihydronaphthalene compound;
and wherein the process comprises production of either 9a 9b

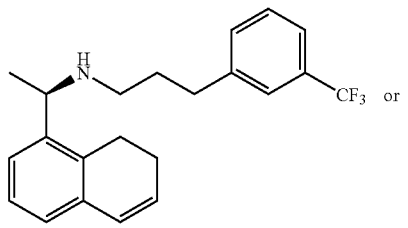 (1)

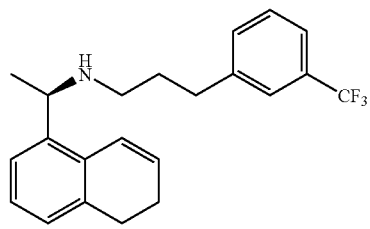 (2)

but not mixtures comprising both (1) and (2).

* * * * *